(12) United States Patent
Loose et al.

(10) Patent No.: US 8,346,491 B2
(45) Date of Patent: Jan. 1, 2013

(54) SONAR-BASED FLOW METER OPERABLE TO PROVIDE PRODUCT IDENTIFICATION

(75) Inventors: Douglas H. Loose, Southington, CT (US); Daniel L. Gysling, Glastonbury, CT (US)

(73) Assignee: Expro Meters, Inc., Wallingford, CT (US)

( * ) Notice: Subject to any disclaimer, the term of this patent is extended or adjusted under 35 U.S.C. 154(b) by 740 days.

(21) Appl. No.: 12/035,826

(22) Filed: Feb. 22, 2008

(65) Prior Publication Data

US 2008/0208483 A1   Aug. 28, 2008

Related U.S. Application Data

(60) Provisional application No. 60/903,244, filed on Feb. 23, 2007.

(51) Int. Cl.
| G01F 1/00 | (2006.01) |
| G01F 7/00 | (2006.01) |
| G01F 22/00 | (2006.01) |
| G01F 1/20 | (2006.01) |

(52) U.S. Cl. .............. 702/45; 702/48; 702/50; 324/306

(58) Field of Classification Search ............ 702/45, 702/47, 48, 50; 324/306, 324–325
See application file for complete search history.

(56) References Cited

U.S. PATENT DOCUMENTS

| 6,354,147 | B1 | 3/2002 | Gysling et al. | |
| 6,401,538 | B1 * | 6/2002 | Han et al. ................. | 73/599 |
| 6,481,288 | B1 | 11/2002 | Humphrey et al. | |
| 6,550,345 | B1 | 4/2003 | Letton | |
| 6,587,798 | B2 | 7/2003 | Kersey et al. | |
| 6,609,069 | B2 | 8/2003 | Gysling | |
| 6,634,239 | B2 | 10/2003 | Gomm et al. | |
| 6,691,584 | B2 | 2/2004 | Gysling et al. | |
| 6,732,575 | B2 | 5/2004 | Gysling et al. | |
| 6,862,920 | B2 | 3/2005 | Gysling et al. | |
| 6,889,560 | B2 * | 5/2005 | Sinha ..................... | 73/861.25 |
| 6,889,562 | B2 | 5/2005 | Gysling et al. | |
| 7,058,549 | B2 | 6/2006 | Gysling et al. | |
| 7,062,976 | B2 | 6/2006 | Gysling et al. | |
| 7,096,719 | B2 | 8/2006 | Gysling | |
| 7,127,360 | B2 | 10/2006 | Gysling et al. | |

(Continued)

FOREIGN PATENT DOCUMENTS

DE    4306119    9/1994

(Continued)

*Primary Examiner* — Cindy H Khuu
*Assistant Examiner* — Ricky Ngon
(74) *Attorney, Agent, or Firm* — O'Shea Getz P.C.

(57) ABSTRACT

An apparatus and method for identifying one or more fluid products flowing within a pipe are provided having a flow meter mounted on the pipe and a processing unit. The flow meter has a plurality of sensors operable to detect vortical disturbances flowing with the fluid products and acoustic waves propagating through the fluid. The sensors produce signals indicative of the vortical disturbances and acoustic waves. The processing unit is operable to determine the speed of sound and volumetric flow rate of the one or more fluid products using the signals from the flow meter. The processing unit includes a database having speed of sound data for a predetermined group of products. The processing unit is operable to identify the type of each product flowing within the pipe given a temperature and pressure value of the products within the pipe.

19 Claims, 18 Drawing Sheets

U.S. PATENT DOCUMENTS

| | | |
|---|---|---|
| 7,146,864 B2 | 12/2006 | Sullivan et al. |
| 7,150,202 B2 | 12/2006 | Gysling |
| 7,261,002 B1 | 8/2007 | Gysling et al. |
| 7,295,933 B2 | 11/2007 | Gysling |
| 7,322,245 B2 | 1/2008 | Gysling et al. |
| 7,331,233 B2 | 2/2008 | Scott |
| 7,340,353 B2 | 3/2008 | Gysling et al. |
| 7,379,828 B2 | 5/2008 | Loose et al. |
| 7,400,985 B2 | 7/2008 | Fernald et al. |
| 7,516,024 B2 | 4/2009 | Gysling |
| 2004/0168522 A1* | 9/2004 | Fernald et al. ............. 73/861.01 |
| 2004/0168523 A1 | 9/2004 | Fernald et al. |
| 2004/0199340 A1* | 10/2004 | Kersey et al. ................... 702/50 |
| 2004/0248307 A1* | 12/2004 | Grof et al. ....................... 436/56 |
| 2005/0011258 A1 | 1/2005 | Gysling et al. |
| 2005/0125170 A1* | 6/2005 | Gysling et al. ................. 702/48 |
| 2006/0048583 A1 | 3/2006 | Gysling |
| 2007/0001028 A1* | 1/2007 | Gysling ........................ 239/318 |
| 2007/0034017 A1* | 2/2007 | Winston et al. ............ 73/861.42 |

FOREIGN PATENT DOCUMENTS

| | | |
|---|---|---|
| GB | 2210169 | 6/1989 |
| WO | 9314382 | 7/1993 |

* cited by examiner

SONAR-BASED FLOW METER OPERABLE TO PROVIDE PRODUCT IDENTIFICATION

CROSS-REFERENCE TO RELATED PATENT APPLICATIONS

This application claims the benefit of U.S. Provisional Patent Application No. 60/903,244 filed Feb. 23, 2007, which is incorporated by reference herein in its entirety.

BACKGROUND OF THE INVENTION

1. Technical Field

This invention relates to methods and apparatus for measuring flow within a conduit (e.g., a pipe) in general, and to the same further operable to identify specific products within the flow in particular.

2. Background Information

Pipelines distributing refined petroleum products are often used for several different products at different times. For example, a pipeline connecting two distribution centers may flow liquefied butane for several hours or days, then switch over to liquefied propane for several hours or days, then switch to butane for another extended period. The tanks which store these different products may be used interchangeably, as well as the manifold and measurement stations at the distribution facilities. Having a method for, and/or an apparatus operable to accurately measure the rate and/or composition of these products, would provide significant utility to the operators of these facilities.

SUMMARY OF THE INVENTION

According to the present invention, an apparatus and method for identifying one or more fluid products flowing within a pipe is provided having a flow meter mounted on the pipe and a processing unit. The flow meter has a plurality of sensors operable to detect vortical disturbances flowing with the fluid products and acoustic waves propagating through the fluid. The sensors produce signals indicative of the vortical disturbances and acoustic waves. The processing unit is operable to determine the speed of sound and volumetric flow rate of the one or more fluid products using the signals from the flow meter. The processing unit includes a database having speed of sound data for a predetermined group of products. The processing unit is operable to identify the type of each product flowing within the pipe given a temperature and pressure value of the products within the pipe.

The invention teaches the use of a sonar-based flow meter to provide at least the volumetric flow rate of product(s) passing through a conduit (e.g., a pipe) and, through the measurement of the sound speed of the product, the identification of the product(s). As shown in the FIGURES, the apparatus may also provide information including the flow rate, mass flow rate, and phase fraction of the fluid.

With the knowledge that certain fluids (e.g., refined liquid hydrocarbons) have well characterized sound speeds, the present invention measures the speed of sound propagating through the fluid to determine (or identify) the fluid (or product) flowing through the pipe. With knowledge of the pressure and temperature of the process fluid, a measurement of the sound speed of the process fluid enables the determination of the type of product flowing through the pipe. For example, at 70 deg F., 150 psi, propane, butane, and decane have sound speeds of 2400 ft/sec, 3000 ft/sec, and 4100 ft/sec respectively. If an operator was dealing with just these three fluids, a database (e.g., a look-up table) could be constructed to identify which product was flowing and when.

The invention involves the inclusion of a data base (e.g., a look-up table) to relate the measured sound speed, alone with pressure and temperature values, into the output of a SONAR-based volumetric flow and sound speed monitor to provide rate and product type identification. The ability of the invention to provide product type information is advantageous not only for fluid flow consisting of a particular product, but also for fluid flow consisting of multiple products. For example, if an operation switches processing one known product to another, the present invention can be configured to provide an estimate of the phase fraction of the two components within a pipe via the Wood Equations. Consequently, the apparatus 10 is operable to determine when and how fast fluids can be transitioned within a pipe. It is anticipated that the real time feedback including product flow rate (including direction) and type will enable more efficient operation of facilities that transport, store, and distribute different fluids (e.g., refined hydro-carbons).

The foregoing and other objects, features and advantages of the present invention will become more apparent in light of the following drawings and detailed description of the present invention.

BRIEF DESCRIPTION OF THE DRAWINGS

Referring now to the drawings, the foregoing and other features and advantages of the present invention will be more fully understood from the following detailed description of illustrative embodiments, taken in conjunction with the accompanying drawings in which like elements are numbered alike.

DETAILED DESCRIPTION OF THE INVENTION

Referring to FIGS. 1-17, the flow monitoring apparatus 10 is similar to that shown and disclosed in U.S. Pat. Nos. 6,354,147; 6,862,920; 7,146,864; 7,058,549, 6,691,584; 6,889,562; 7,062,976; 7,127,360; 7,150,202; 7,197,942; and 7,295,933, and U.S. patent application Ser. Nos. 10/875,858, 10/712,818, 10/712,833, and 11/205,899, which are all incorporated herein by reference.

Figure 1:
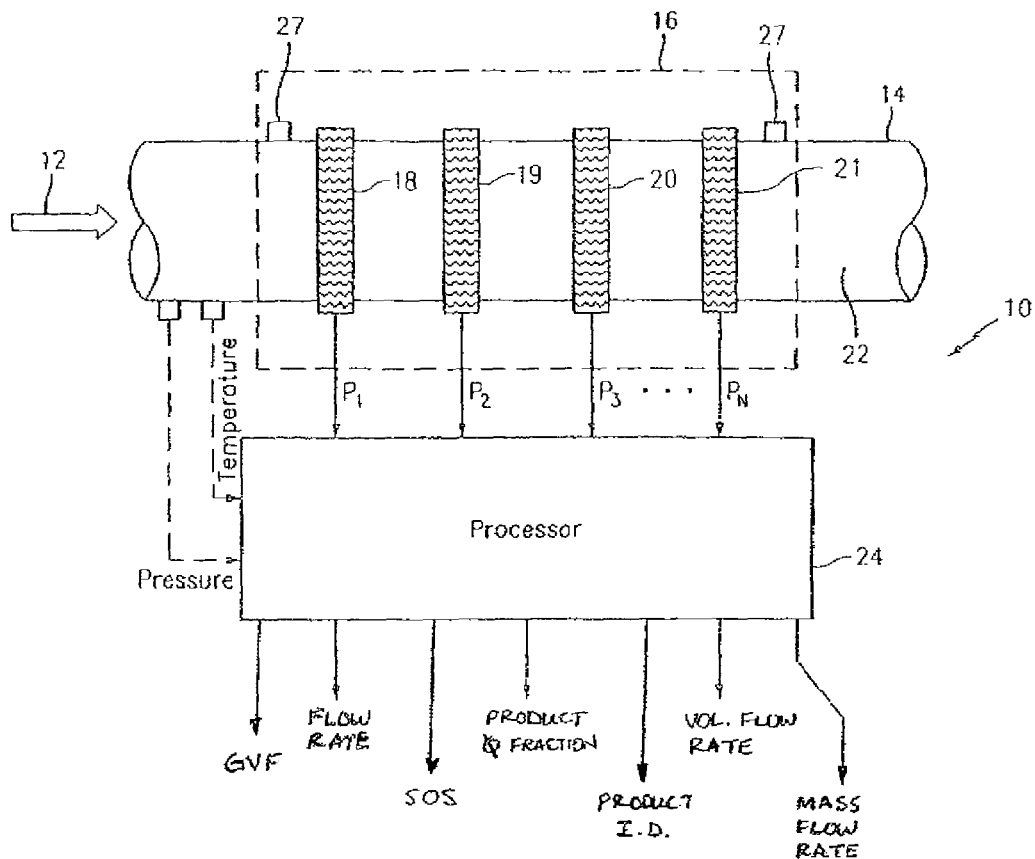
FIG. 1 is schematic diagram of an apparatus for measuring at least the velocity of the fluid flowing through a pipe and for identifying the fluid in the pipe in accordance with the present invention.
Figure 2:
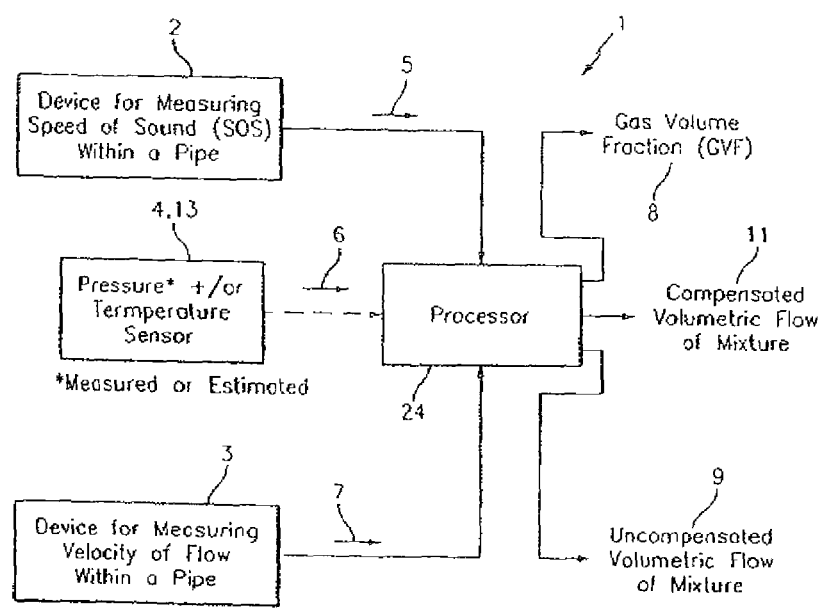
FIG. 2 is a block diagram of an embodiment of at least a portion of the apparatus of FIG. 1.

FIG. 2 is a block diagram 1 of the apparatus 10 of FIG. 1 that includes a device 2 for measuring the speed of sound (SOS) propagating within a pipe 14 and a device 3 for measuring the velocity of the mixture 12 within the pipe 14. A pressure sensor 4 and/or temperature sensor 13 measures the pressure and/or temperature of the mixture flowing through the pipe. Alternatively, the pressure and/or temperature may be input or estimated rather than actually measured. In response to the speed of sound signal 5, the velocity 7 of the flow 12 and characteristics 6 of the flow (e.g., pressure and temperature), a processor 24 determines flow parameters such as the gas volume fraction (GVF) of the flow 12, the uncompensated volumetric flow 9 of the mixture, and the volumetric flow 11 of the flow compensated for the entrained air therein, etc.

Figure 3:
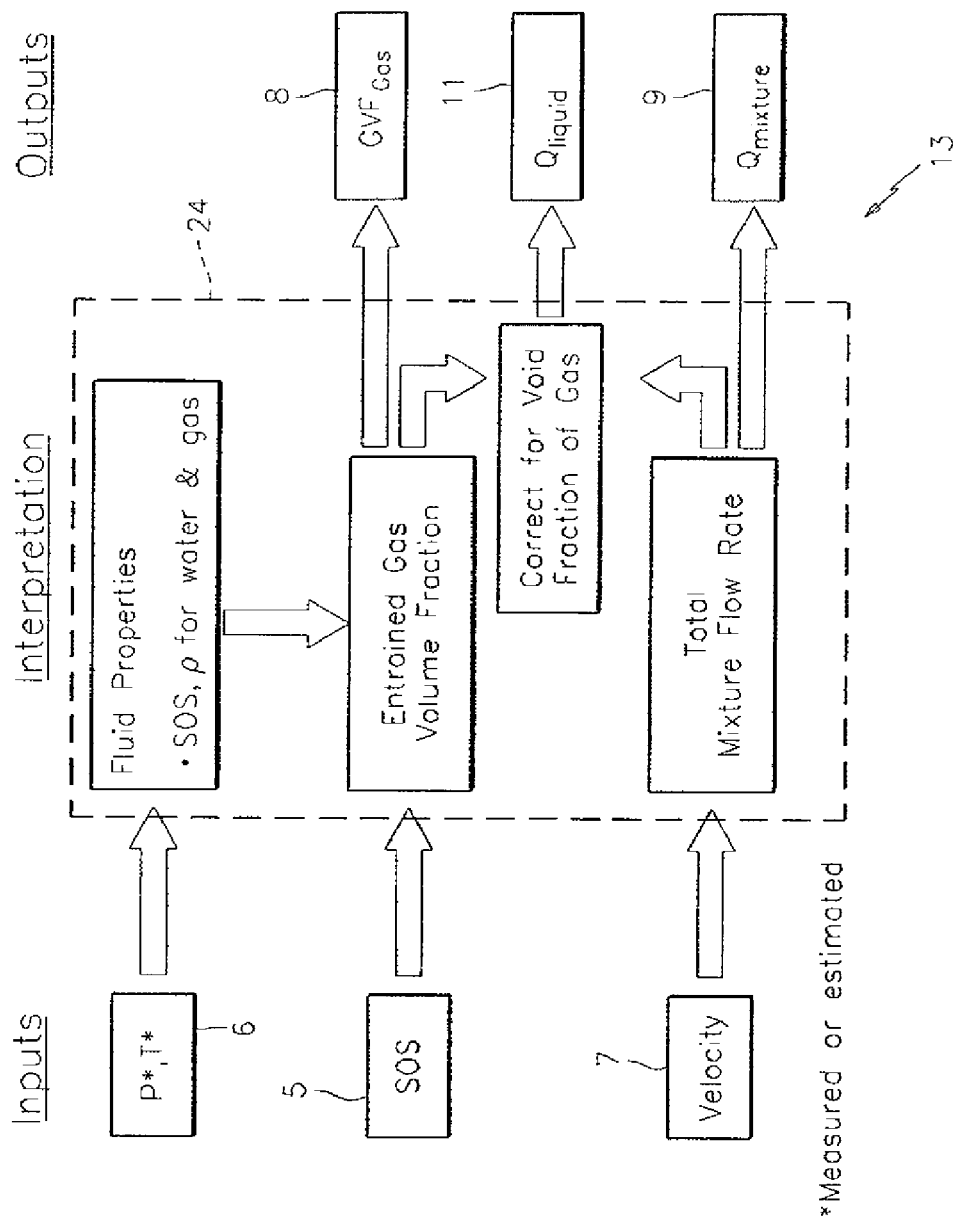
FIG. 3 is a functional flow diagram of an apparatus embodying certain functions associated with the processor of an apparatus such as that shown in FIG. 1.

A flow chart 13 shown in FIG. 3 illustrates certain functions of the processor 24. As shown in FIG. 2, the inputs to the processor include the speed of sound (SOS) within the pipe 14, the velocity 7 of the mixture 12, and the pressure and temperature 6 of the mixture. The fluid properties of the mixture (e.g., SOS and density) are determined knowing the pressure and temperature of the mixture. The gas volume fraction of the mixture (GVF) is determined using the SOS measurement and fluid properties, which will be described in greater detail hereinafter. The volumetric flow rate of the mixture (including any entrained gas) is determined using the velocity and knowing the cross-sectional area of the inner diameter of the pipe. The processor 24 provides a compensated volumetric flow measurement of the mixture by correcting the uncompensated volumetric flow rate using the void fraction of the air.

Figure 4:
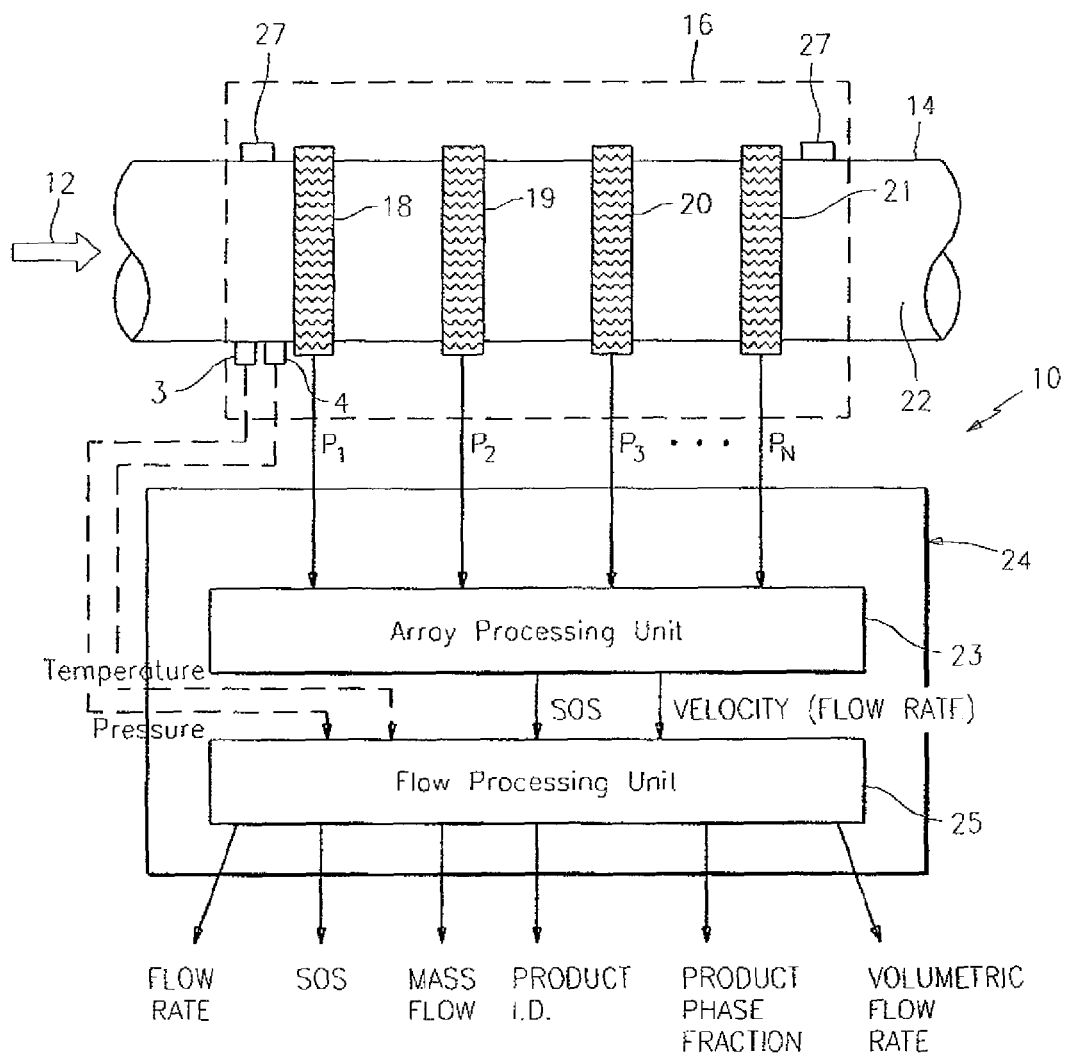
FIG. 4 is a more detailed schematic diagram of the apparatus of FIG. 1.
Figure 5:
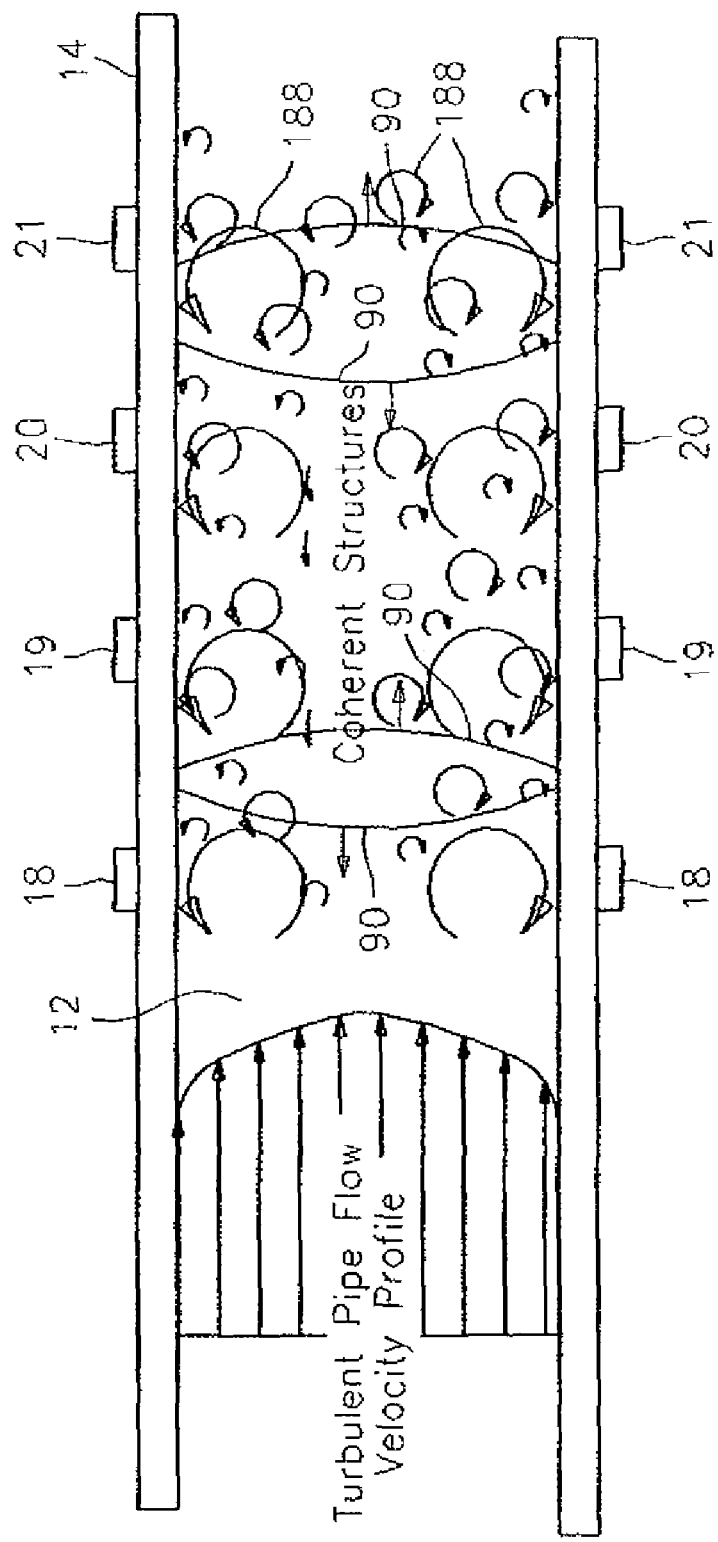
FIG. 5 is a cross-sectional view of a pipe having coherent structures therein.

Now referring to FIGS. 1 and 4, the apparatus 10 includes a sensing device 16 for sensing a process flow 12 passing within an interior passage of a conduit 14 (e.g., a pipe), and a processor 24. The sensing device 16 includes an array of two or more pressure sensors (or transducers) 18-21 spaced axially along an outer surface 22 of the pipe 14. The sensing device 16 shown in FIGS. 1 and 2 has an array of "N" number of sensors 18-21, where "N" is an integer equal to or greater than 2. In some embodiments, the pressure sensors 18-21 measure pressure or strain within the pipe 14 created by vortical disturbances 188 and/or acoustic waves 90 propagating with or through the fluid 12 as shown in FIG. 5; i.e., unsteady pressure $P_1$-$P_N$ of the fluid 2 flowing through the pipe. The pressure sensors 18-21 may be ported or clamp-on sensors; e.g., as described in the above-referenced U.S. patents and U.S. patent applications. The output signals ($P_1$-$P_N$) of the pressure sensors 18-21 are provided to the processing unit 24, which processes the unsteady pressure measurement data along with static pressure and temperature of the flow to determine at least one parameter of the flow; e.g., flow rate, volumetric flow rate, mass flow rate, phase fraction, speed of sound, and product information.

In some embodiments, each of the pressure sensors may include a piezoelectric film sensor to measure the unsteady pressures of the flow 12 using techniques such as those described above. The piezoelectric film sensors may each include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc. The piezoelectric film sensors are similar to that described in U.S. patent application Ser. No. 10/712,833, which is incorporated herein by reference.

Now referring to FIGS. 17 and 18a-18c, in still other embodiments each pressure sensor 18-21 may be a sensing unit that includes a pair of ultrasonic sensors 40, 42, one of which ultrasonic sensors acts as a transmitter (Tx) and the other acts as a receiver (Rx). The pair of sensors 40, 42 may be diametrically disposed on the pipe (i.e., normal to the pipe) at predetermined locations along the pipe to provide a through transmission configuration (e.g., see FIG. 17), such that the sensors transmit and receive an ultrasonic signal that propagates through the fluid substantially orthogonal to the direction of the flow of the fluid within the pipe. In alternative arrangements, the transmitter and receiver of each pressure sensor may be arranged in configurations including, but not limited to: 1) diametrically opposed to one another, with an axial offset (FIG. 18a); 2) side-by-side in a pulse/echo configuration, wherein the receiver senses reflected signal (FIG. 18b); 3) disposed on the same side of the pipe in a pitch and catch configuration (FIG. 18c), etc. An example of an acceptable ultrasonic sensor for use as a pressure sensor 18-21 is Krautkramer Model No. 113-241-591 manufactured by Krautkramer Ultrasonic Systems of Lewistown, Pa., U.S.A. A more detailed description of these sensor configurations is provided in U.S. patent application Ser. No. 10/756,977, filed Jan. 13, 2004, which is hereby incorporated by reference in its entirety.

Figure 17:
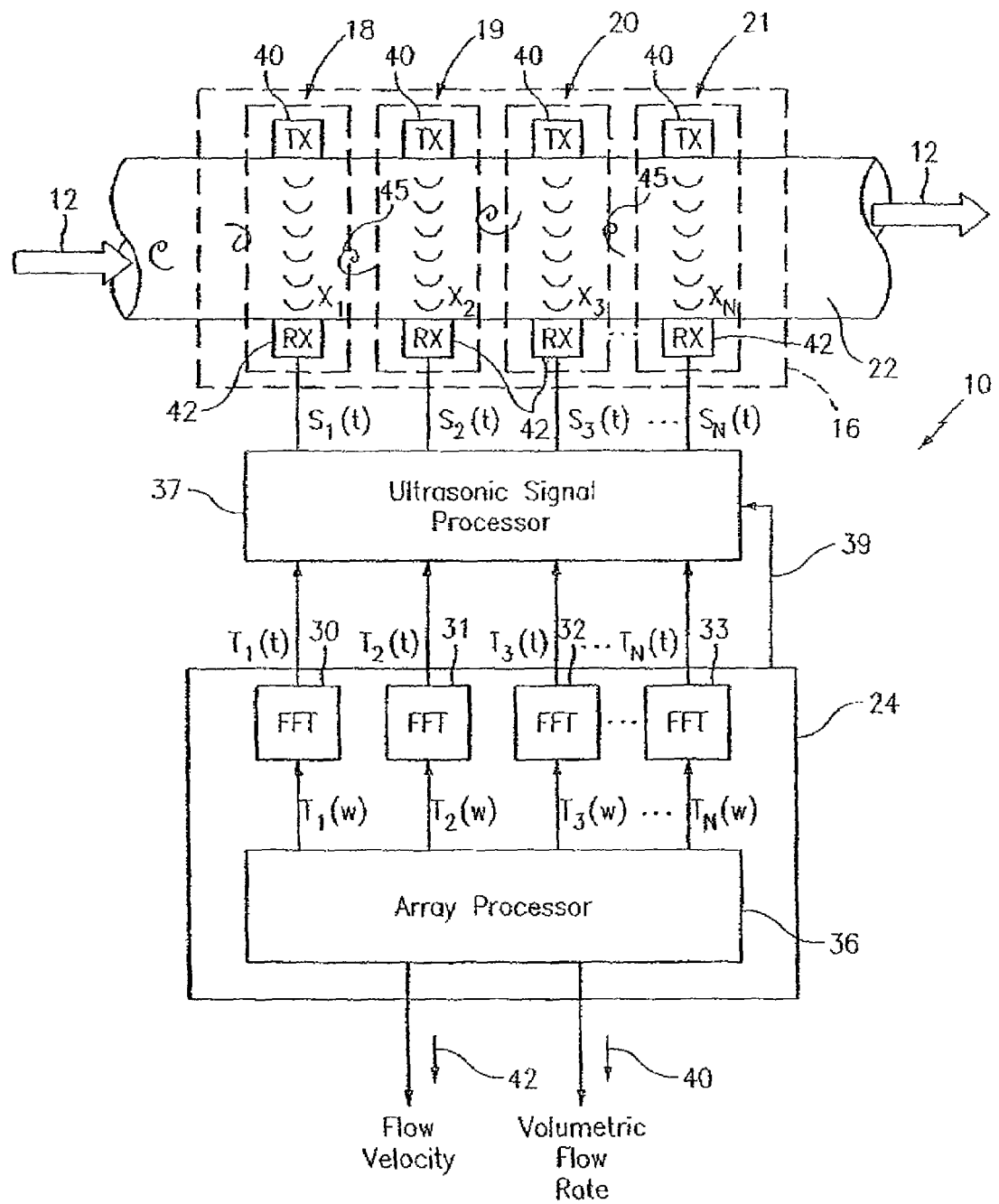
FIG. 17 is a block diagram of a flow meter having an array of ultrasonic sensor units disposed axially along a pipe for measuring the volumetric flow of the fluid flowing in the pipe.
Figure 18A:
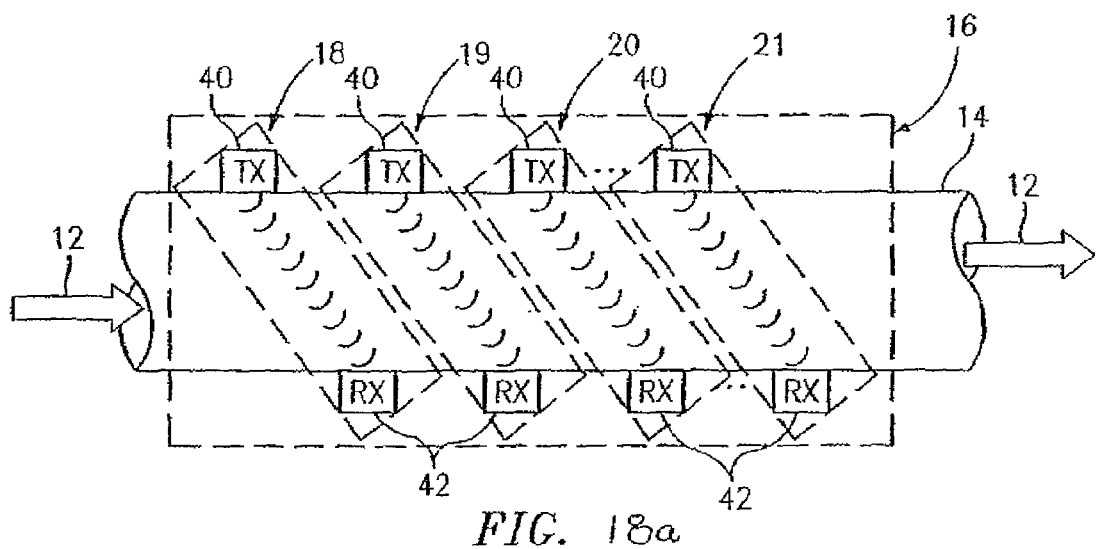
FIG. 18a is a block diagram of an alternative embodiment of a sensing device of a flow meter embodying the present invention similar to that shown in FIG. 17.
Figure 18B:
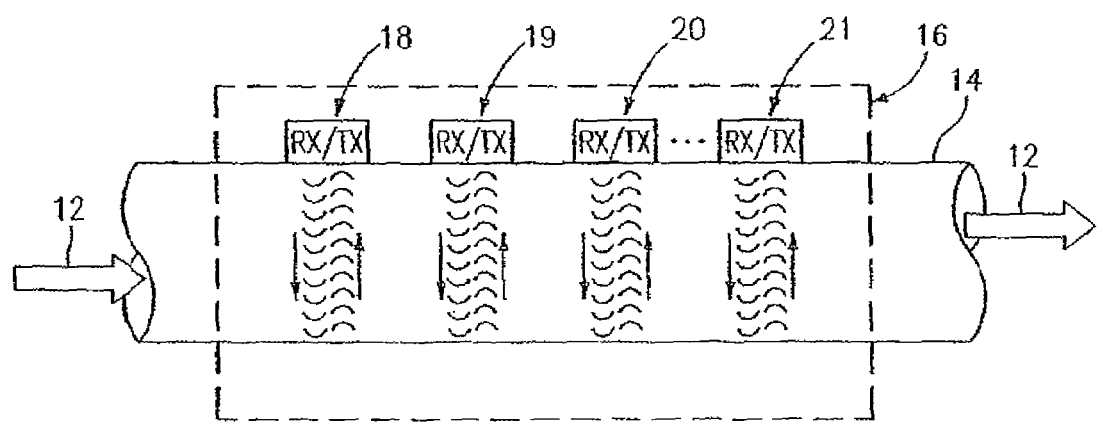
FIG. 18b is a block diagram of an alternative embodiment of a sensing device of a flow meter embodying the present invention similar to that shown in FIG. 17.
Figure 18C:
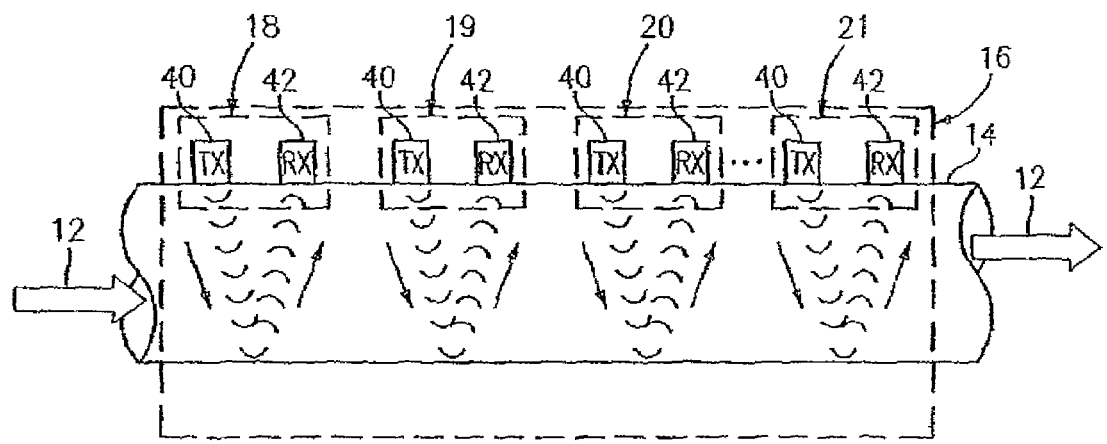
FIG. 18c is a block diagram of an alternative embodiment of a sensing device of a flow meter embodying the present invention similar to that shown in FIG. 17.

As shown in FIG. 17, each pair of ultrasonic sensors 40, 42 measures a transit time (i.e., time of flight (TOF), or phase modulation) of an ultrasonic signal propagating through the fluid 12 from the transmitting sensor 40 to the receiving sensor 42. The transit time measurement or variation is indicative of a coherent properties that convect with the flow within the pipe (e.g., vertical disturbances, inhomogenieties within the flow, temperature variations, bubbles, particles, pressure disturbances), which are indicative of the velocity of the process flow 12. The ultrasonic sensors may operate at any frequency, however, it has be found that the higher frequency sensors are more suitable for single phase fluids while lower frequency sensors are more suitable for multiphase fluids. The optimum frequency of the ultrasonic sensor is dependent on the size or type of particle or substance propagating with the flow 12. For instance, the larger the air bubbles in an aerated fluid the lower the desirable frequency of the ultrasonic signal. Examples of frequency used for a flow meter embodying the present invention are 1 MHz and 5 MHz. The ultrasonic sensors may also provide a pulsed, chirped or continuous signal through the fluid flow 12.

An ultrasonic signal processor 37 fires the sensors 40 in response to a firing signal 39 from the transmitter 24 and receives the ultrasonic output signals $S_1(t)$-$S_N(t)$ from the sensors 42. The signal processor 37 processes the data from each of the sensor units 18-21 to provide an analog or digital output signal $T_1(t)$-$T_N(t)$ indicative of the time of flight or transit time of the ultrasonic signal through the fluid. The signal processor 37 may also provide an output signal indicative of the amplitude (or attenuation) of the ultrasonic signals. One such signal processor is model no. USPC 2100 manufactured by Krautkramer Ultrasonic Systems. Measuring the amplitude of ultrasonic signal is particularly useful and works best for measuring the velocity of a fluid that includes a substance in the flow (e.g., multiphase fluid or slurry).

The output signals ($T_1(t)$-$T_N(t)$) of the ultrasonic signal processor 37 are provided to the processor 24, which processes the transit time measurement data to determine the volumetric flow rate. The transit time or time of flight measurement is defined by the time it takes for an ultrasonic signal to propagate from the transmitting sensor 40 to the respective receiving sensor 42 through the pipe wall and the fluid 12. The effect of the vortical disturbances 45 (and/or other inhomogenities within the fluid) on the transit time of the ultrasonic signal is to delay or speed up the transit time. Therefore, each sensing unit 18-21 provides a respective output signal $T_1(t)$-$T_N(t)$ indicative of the variations in the transit time of the ultrasonic signals propagating orthogonal to the direction of the fluid 12. The measurement is derived by interpreting the convecting coherent property and/or characteristic within the process piping using at least two sensor units 18, 19. The velocity of the vortical disturbances is related to the velocity of the flow 12 and hence the volumetric flow rate may be determined. The ultrasonic sensors 18-21 may be "wetted" or clamped onto the outer surface 22 of the pipe 14 (e.g. contact or non-contact sensor).

The apparatus 10 has the ability to measure the volumetric flow rate and other flow parameters using one or both of the following techniques: 1) determining the speed of sound of acoustical disturbances or sound waves propagating through the flow 12 using the array of pressure sensors 18-21; and/or 2) determining the velocity of vortical disturbances or "eddies" traveling within the flow 12 using the array of pressure sensors 18-21. Generally, the first technique measures the unsteady pressures created by acoustical disturbances propagating through the flow 12 to determine the speed of sound (SOS) propagating through the flow. By knowing (e.g., by measurement or estimation) the pressure and/or temperature of the flow and determining the speed of sound of the acoustical disturbances, the processing unit 24 can determine flow parameters such as the mass flow rate, the consistency of the mixture (i.e., the mass/air ratio, the mass/liquid ratio, the liquid/air ratio), the volumetric flow rate, the density of the mixture, the enthalpy of the mixture, the Mach number of the mixture, and other parameters. One or more acoustic sources 27 may be included (e.g., at the input end, output end, or both ends of the array) to facilitate the measurement of the speed of sound propagating through the flow 12 for instances of acoustically quiet flow. The second technique measures the velocities associated with unsteady flow fields and/or pressure disturbances created by vortical disturbances or "eddies" 188 (see FIG. 5) to determine the velocity of the flow 12. The pressure sensors 18-21 measure the unsteady pressures $P_1$-$P_N$ created by the vortical disturbances as these disturbances convect within the flow 12 through the pipe 14 in a known manner. The velocity of these vortical disturbances is related to the velocity of the mixture and hence the volumetric flow rate may be determined.

Figure 6:
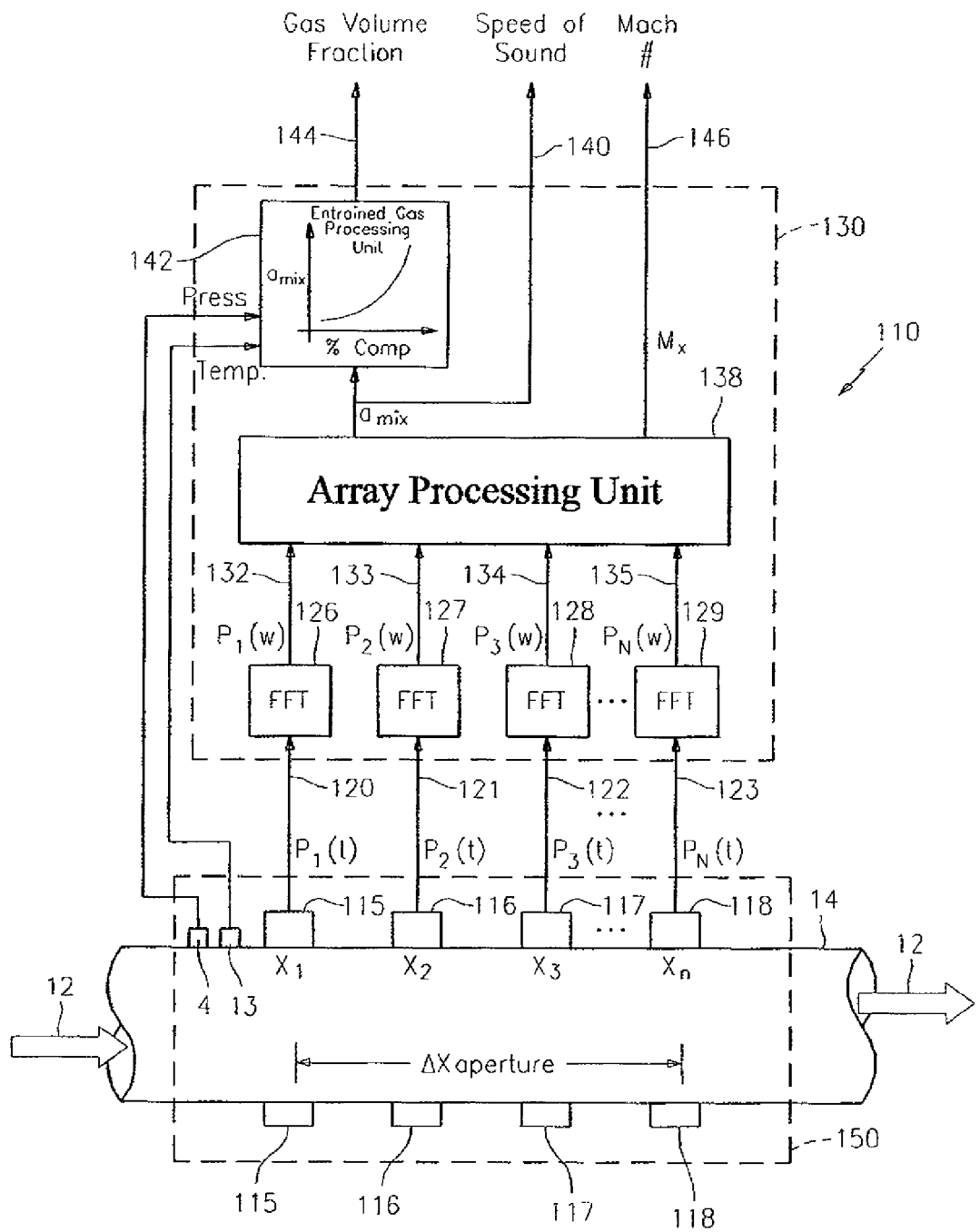
FIG. 6 is a block diagram of an apparatus for measuring the speed of sound propagating through a process flow flowing within a pipe, in accordance with the present invention.

Now referring to FIG. 6, the apparatus 10 is operable to measure the speed of sound (SOS) of one-dimensional sound waves propagating through the fluid to determine fluid flow parameters such as gas volume fraction (GVF), speed of sound (SOS), and Mach number. It is known that sound propagates through various mediums at various speeds in such fields as SONAR and RADAR fields. The speed of sound propagating through the pipe and mixture 12 may be determined using a number of known techniques, such as those set forth in U.S. Pat. Nos. 6,354,147; 6,609,069; and 6,587,798, U.S. Pat. No. 6,732,575, each of which are incorporated herein by reference.

In accordance with the present invention, the speed of sound propagating through the flow 12 is measured by passively listening to the flow with an array of unsteady pressure sensors to determine the speed at which one-dimensional compression waves propagate through the flow 12. As shown in FIG. 6, an apparatus 10 measuring the speed of sound in the mixture 12 has an array of at least two acoustic pressure sensors 115, 116, 117, 118 located at two locations $x_1$, $x_2$, $x_3$, ... $x_N$ axially along the pipe 14. The pressure sensors 115-118 measure the unsteady pressures generated by the acoustic waves, and in response provide pressure time-varying signals $P_1(t)$, $P_2(t)$, $P_3(t)$, ... $P_N(t)$ on lines 120, 121, 122, 123 to a signal processing unit 24 to known Fast Fourier Transform (FFT) logics 126, 127, 128, 129, respectively. The FFT logics 126-129 calculate the Fourier transform of the time-based input signals $P_1(t)$-$P_N(t)$ and provide complex frequency domain (or frequency based) signals $P_1(\omega)$, $P_2(\omega)$, $P_3(\omega)$, ... $P_N(\omega)$ on lines 132, 133, 134, 135 indicative of the frequency content of the input signals. Other techniques for obtaining the frequency domain characteristics of the signals $P_1(t)$-$P_N(t)$ may be used instead of FFTs. For example, the cross-spectral density and the power spectral density may be used to form a frequency domain transfer function (or frequency response or ratios).

The frequency signals $P_1(\omega)$-$P_N(\omega)$ are fed to array processing unit 138 which provides a signal to line 140 indicative of the speed of sound of the mixture $a_{mix}$ (discussed more hereinafter). The $a_{mix}$ signal is provided to map (or equation) logic 142, which converts $a_{mix}$ to a percent composition of a mixture and provides a % Comp signal to line 144 indicative thereof More specifically, for planar one-dimensional acoustic waves in a homogenous mixture, it is known that the acoustic pressure field $P(x,t)$ at a location x along the pipe 14, where the wavelength λ of the acoustic waves to be measured is long compared to the diameter "d" of the pipe 14 (i.e., $\lambda/d \gg 1$), may be expressed as a superposition of a right traveling wave and a left traveling wave, as follows:

$$P(x,t) = (Ae^{-ik_r x} + Be^{ik_l x})e^{i\omega t} \quad \text{Eqn. 1}$$

where A, B are the frequency-based complex amplitudes of the right and left traveling waves, respectively, x is the pressure measurement location along a pipe 14, $\omega$ is frequency (in rad/sec, where $\omega = 2\pi f$), and $k_r$, $k_l$ are wave numbers for the right and left waves, respectively, which are defined as:

$$k_r \equiv \left(\frac{\omega}{a_{mix}}\right)\frac{1}{1+M_x} \text{ and } k_l \equiv \left(\frac{\omega}{a_{mix}}\right)\frac{1}{1-M_x} \quad \text{Eqn. 2}$$

where $a_{mix}$ is the speed of sound of the mixture in the pipe, $\omega$ is frequency (in rad/sec), and $M_x$ is the axial Mach number of the flow of the mixture within the pipe, where:

$$M_x \equiv \frac{V_{mix}}{a_{mix}}$$

where $V_{mix}$ is the axial velocity of the mixture. For non-homogenous mixtures, the axial Mach number represents the average velocity of the mixture and the low frequency acoustic field description remains substantially unaltered.

The data from the array of sensors 115-118 may be processed in any domain, including the frequency/spatial domain, the temporal/spatial domain, the temporal/wavenumber domain or the wave-number/frequency (k-$\omega$) domain. As such, any known array processing technique in any of these or other related domains may be used if desired, similar to the techniques used in the fields of SONAR and RADAR.

Figure 7:
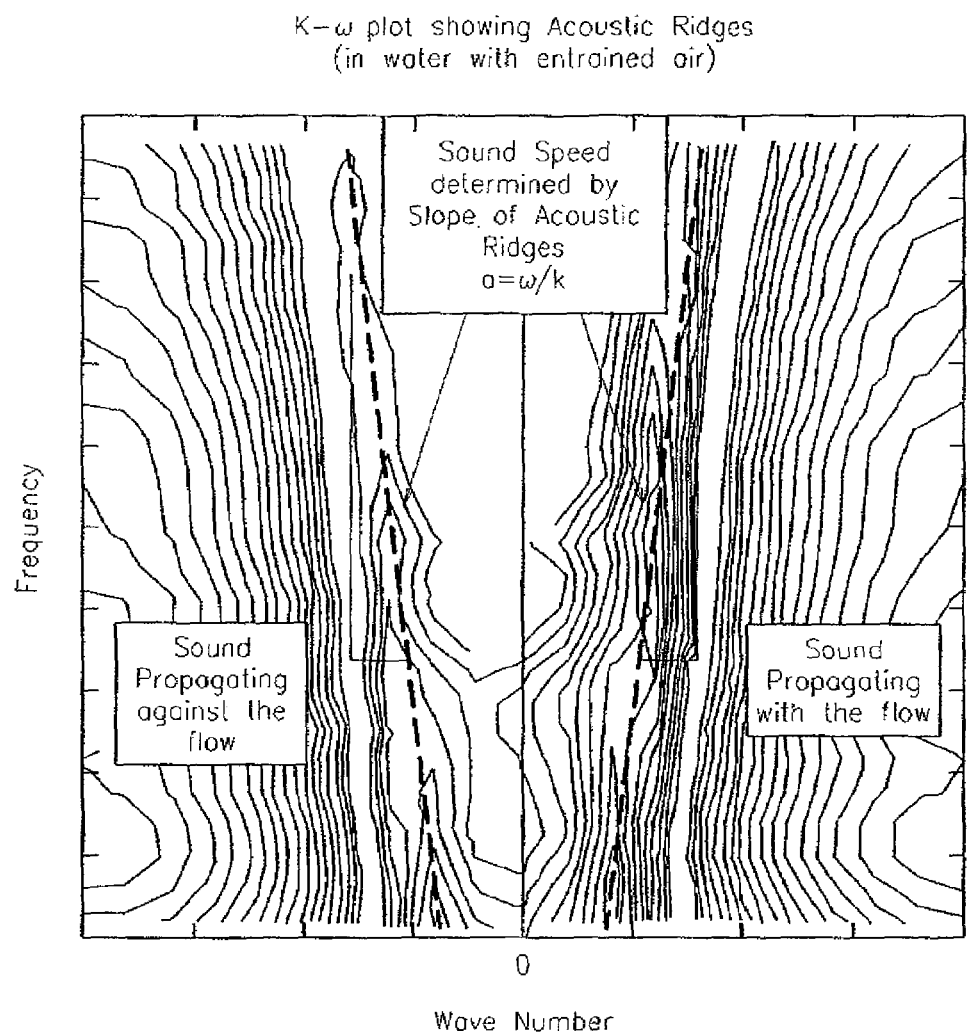
FIG. 7 is a k-ω plot of data processed from the apparatus of the present invention that illustrates the slope of the acoustic ridge, in accordance with the present invention.

One such technique of determining the speed of sound propagating through the flow 12 is using array processing techniques to define an acoustic ridge in the k-$\omega$ plane as shown in FIG. 7. The slope of the acoustic ridge is indicative of the speed of sound propagating through the flow 12. This technique is similar to that described in U.S. Pat. No. 6,587,798 filed Nov. 28, 2001, titled "Method and System for Determining the Speed of Sound in a Fluid Within a Conduit", which is incorporated herein by reference. The speed of sound (SOS) is determined by applying sonar arraying processing techniques to determine the speed at which the one dimensional acoustic waves propagate past the axial array of unsteady pressure measurements distributed along the pipe 14.

The signal processor 24 performs a Fast Fourier Transform (FFT) of the time-based pressure signals $P_1(t)$-$P_N(t)$ to convert the pressure signal into the frequency domain. The power of the frequency-domain pressure signals is then determined and defined in the k-$\omega$ plane by using array processing algorithms (e.g., Capon or Music algorithms). The acoustic ridge in the k-$\omega$ plane, as shown in the k-$\omega$ plot of FIG. 7, is then determined. The speed of sound (SOS) is determined by measuring slope of the acoustic ridge. The gas volume fraction can then be calculated or otherwise determined.

Referring back to FIGS. 1 and 4, the flow meter of the present invention uses known array processing techniques, in particular the Minimum Variance, Distortionless Response (MVDR, or Capon technique), to identify pressure fluctuations, which convect with the materials flowing in a conduit and accurately ascertain the velocity, and thus the flow rate, of said material. These processing techniques utilize the covariance between multiple sensors 18-21 at a plurality of frequencies to identify signals that behave according to a given assumed model; in the case of the apparatus 10, the model represents pressure variations convecting at a constant speed across the pressure sensors comprising the flow meter monitoring head 12.

To calculate the power in the k-$\omega$ plane, as represented by a k-$\omega$ plot (see FIG. 7) of either the pressure signals, the processor 24 determines the wavelength and so the (spatial) wavenumber k, and also the (temporal) frequency and so the angular frequency $\omega$ of various spectral components of the acoustic waves created passively or actively within the pipe. There are numerous algorithms available in the public domain to perform the spatial/temporal decomposition of arrays of sensor units 18-21.

In the case of suitable acoustic pressures being present, the power in the k-$\omega$ plane shown in a k-$\omega$ plot of FIG. 7 so determined will exhibit a structure that is called an acoustic ridge associated with sound propagating with the flow and one associated with sound propagating against the flow. The acoustic ridge represents the concentration of the disturbances that propagate with and against the flow and is a mathematical manifestation of the relationship between the spatial variations and temporal variations described above. Such a plot will indicate a tendency for k-$\omega$ pairs to appear more or less along a line with some slope, the slope indicating the speed of sound traveling in both directions. The power in the k-$\omega$ plane so determined is then provided to an acoustic ridge identifier, which uses one or another feature extraction method to determine the location and orientation (i.e., slope) of any acoustic ridge present in the k-$\omega$ plane. Finally, information including the acoustic ridge orientation (i.e., slope) is used by an analyzer to determine the speed of sound.

The array processing unit 23 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. The beam forming or array processing algorithms transform the time domain signals from the sensor array into their spatial and temporal frequency components, i.e. into a set of wave numbers given by $k = 2\pi/\lambda$ where $\lambda$ is the wavelength of a spectral component, and corresponding angular frequencies given by $\omega = 2\pi v$.

The prior art teaches many algorithms operable to spatially and temporally decompose a signal from a phased array of sensors, and the present invention is not restricted to any particular algorithm. Acceptable adaptive array processing algorithms include the Capon method/algorithm and the MUSIC algorithm. The present invention recognizes that such techniques can be used to determine speed of sound propagating through the fluid 12.

Also, some or all of the functions within the processor 24, 130, 174 may be implemented in software (using a microprocessor or computer) and/or firmware, or may be implemented using analog and/or digital hardware, having sufficient memory, interfaces, and capacity to perform the functions described herein.

It is within the scope of the present invention that the pressure sensor spacing may be known or arbitrary and that as few as two sensors are required if certain information is known about the acoustic properties of the process flow 12. The pressure sensors are spaced sufficiently such that the entire length of the array (aperture) is at least a significant fraction of the measured wavelength of the acoustic waves being measured. The acoustic wavelength is a function of the type or characteristics of flow 12.

Now referring back to FIG. 6, the apparatus 110 utilizes similar processing algorithms as those employed for the volumetric flow measurement to also measure sound speed. As with convective disturbances, the temporal and spatial frequency content of sound propagating within the process piping is related through a dispersion relationship.

$$k = \frac{\omega}{a_{mix}}$$

As before, k is the wave number, defined as $k=2\pi/\lambda$, $\omega$ is the temporal frequency in rad/sec, and $a_{mix}$ is the speed at which sound propagates within the process piping. Unlike disturbances, which convect with the flow, however, sound generally propagates in both directions; i.e., with and against the mean flow. For these cases, the acoustic power is located along two acoustic ridges, one for the sound traveling with the flow at a speed of $a_{mix}+V_{mix}$ and one for the sound traveling against the flow at a speed of $a_{mix}-V_{mix}$.

FIG. 7 shows a k-$\omega$ plot generated for acoustic sound field recorded from water flowing at a rate of 240 gpm containing ~2% entrained air by volume in a 3 inch diameter, schedule 10, stainless steel pipe. The k-$\omega$ plot was constructed using data from an array of strain-based sensors attached to the outside of the pipe. Two acoustic ridges are clearly evident. Based on the slopes of the acoustic ridges, the sound speed for this mixture was about 330 ft/sec (100 m/s), consistent with that predicted by the Wood Equations.

While the sonar-based flow meter using an array of sensors can be used to measure the speed of sound of an acoustic wave propagating through the mixture, one will appreciate that any means for measuring the speed of sound of the acoustic wave may be used to determine the entrained air volume fraction of the mixture/fluid. For example, there may be advantages to using ultrasonic sensors to measure the SOS in the presence of entrained gas. An array of low frequency pressure sensors (,~1000 kHz) will track mainly with entrained gas content via the Wood Equations. Ultrasonic sensors (~>100 kHz) used to measure high frequency SOS will be relatively insensitive to entrained gases and will represent the SOS of liquid components. The apparatus 110 further includes the ability to measure a volumetric flow rate of the mixture by comparing the difference of the speed of one dimensional sound waves propagating with and against the mean flow.

This method of determining the volumetric flow rate of the flow 12 relies on the interaction of the mean flow with the acoustic pressure field. The interaction results in sound waves propagating with the mean flow traveling at the speed of sound plus the convection velocity and, conversely, sound waves traveling against the mean flow propagating at the speed of sound minus the convection velocity. That is, $$a_R = a_{mix} + u \quad a_l = a_{mix} - u$$

where $a_R$ equals the velocity of a right traveling acoustic wave relative to a stationary observer (i.e. the pipe 14), $a_L$ equals the velocity of a left traveling acoustic wave apparent to a stationary observer, $a_{mix}$ equals the speed of sound traveling through the mixture (if the mixture was not flowing), and u equals the mean flow velocity (assumed to be flowing from left to right in this instance). Combining these two equations yields an equation for the mean velocity:

$$u = \frac{a_R - a_L}{2}$$

Therefore, by measuring the propagation velocity of acoustic waves in both directions relative to the pipe 14 as described hereinbefore, the mean flow velocity can be calculated by multiplying the mean flow velocity by the cross-sectional area of the pipe 14.

Further, FIG. 7 illustrates the ability of the present invention to determine the velocity of a fluid moving in a pipe. The contours represent the relative signal power at all combinations of frequency and wavenumber. The highest power "ridges" represent the acoustic wave with slope of the ridges equal to the propagation speed. The dashed lines show the best-fit two-variable maximization of the power with the two variables being sound speed and flow velocity. The right-side ridge represents the acoustic wave traveling in the same direction as the bulk flow and therefore its slope is steeper than the left-side ridge that represents the acoustic wave traveling in the opposite direction of the flow. This indicates that the acoustic wave traveling in the same direction of the flow is traveling faster than the acoustic wave traveling in the opposite direction of the flow relative to the stationary sensors located on the probe.

As indicated above, the apparatus 10 of FIGS. 1 and 4 embodying the present invention also includes the ability to measure volumetric flow rate of the mixture by measuring the unsteady pressures generated by vortical disturbances 188 propagating in the mixture 12 (see FIG. 5). The apparatus 10 uses one or both of the following techniques to determine the convection velocity of the vortical disturbances within the process flow 12 by: 1) characterizing the convective ridge of the vortical disturbances using an array of unsteady pressure sensors; and 2) cross-correlating unsteady pressure variations using an array of unsteady pressure sensors.

To measure volumetric flow, the sonar meter characterizes speed at which coherent vortical structures convect past an axial array of sensors using beam forming techniques developed over several decades for underwater acoustic application. Coherent structures are an inherent feature of turbulent boundary layers present in all turbulent flows. Unlike conventional vortex shedding meters, no internal geometry is required to generate these structures.

The overwhelming majority of industrial process flows involve turbulent flow 12. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar based array processing flow metering technology, understanding the time-averaged velocity profile in turbulent flow 12 provides a means to interpret the relationship between speed at which coherent structures 118 convect and the volumetrically averaged flow rate.

Turbulent pipe flows 12 are highly complex flows. Predicting the details of any turbulent flow is problematic. Much is known, however, regarding the statistical properties of the flow. For instance, turbulent flows contain turbulent eddies 188 (i.e., self-generating, coherent vortica structures). The maximum length scale of the eddies 188 is set by the diameter of the pipe 14. The eddies 188 remain coherent for several tube diameters downstream, eventually breaking down into progressively smaller eddies until the energy is dissipated by viscous effects. Experimental investigations have established that eddies generated within turbulent boundary layers convect at roughly 80% of maximum flow velocity. For pipe flows, this implies that turbulent eddies will convect at approximately the volumetrically averaged flow velocity within the pipe 14. The precise relationship between the convection speed of turbulent eddies and the flow rate for each class of meters can be calibrated empirically.

FIG. 5 diagrammatically illustrates the relevant flow features of turbulent pipe flow 12 along with an axial array of sensors 18-21. As shown, the time-averaged axial velocity is a function of radial position, from zero at the wall to a maximum at the centerline of the pipe. The flow 12 near the wall is characterized by steep velocity gradients and transitions to relatively uniform core flow near the center of the pipe 14. The turbulent eddies are superimposed over the time averaged velocity profile.

From a volumetric flow measurement perspective, the volumetrically averaged flow velocity is of interest. The volumetrically averaged flow velocity, defined as the total volumetric flow rate, Q, divided by the cross sectional area of the conduit, A, is a useful, but arbitrarily defined property of the flow. In fact, given the velocity profile within the pipe, little flow is actually moving at this speed. The precise relationship between the convection speed of turbulent eddies and the flow rate is determined experimentally through calibration for each.

The Reynolds number (Re), based on pipe diameter (D), characterizes many of the engineering properties of the flow. The Reynolds number is a non-dimensional ratio representing the relative importance of inertial forces to viscous forces within a flow:

$$Re = \frac{\text{inertial}}{\text{viscous}} \text{ forces} = \frac{\rho u \frac{\partial u}{\partial x}}{\mu \frac{\partial^2 u}{\partial y^2}} = \frac{UD}{\nu}$$

where $\rho$ is the fluid density, $\mu$ is the dynamic viscosity, U is the volumetrically averaged flow velocity and $\nu$ ($=\mu/\rho$) is the kinematic viscosity.

The critical Reynolds number for pipe flows, above which flows are considered turbulent, is ~2300. Most flows in the paper and pulp industry have a Reynolds number ranging from one hundred thousand to several million, well within the turbulent regime. In addition to demarcating a boundary between laminar and turbulent flow regimes, the Reynolds number is a similarity parameter for pipe flows, i.e. flows in geometrically similar pipes with the same Reynolds number are dynamically similar (Schlichting p. 12).

The first technique of determining the convection velocity of the vortical disturbances within the flow 12 is by characterizing the convective ridge of the vertical disturbances using an array of unsteady pressure sensors, similar to that shown in U.S. Pat. No. 6,609,069, filed Dec. 4, 2000, entitled "Method and Apparatus for Determining the Flow Velocity Within a Pipe", which is incorporated herein by reference.

The sonar flow metering methodology uses the convection velocity of a coherent structure with turbulent pipe flows 12 to determine the volumetric flow rate. The convection velocity of these eddies 188 is determined by applying sonar arraying processing techniques to determine the speed at which the eddies convect past an axial array of unsteady pressure measurements distributed along the pipe 14, similar to the technique described for the apparatus 110 of FIG. 6 for measuring gas volume fraction with a fluid.

The sonar-based algorithms determine the speed of the eddies 188 by characterizing both the temporal and spatially frequency characteristics of the flow field. For a series of coherent eddies convecting past a fixed array of sensors, the temporal and spatial frequency content of pressure fluctuations are related through the following relationship:

$$k = \frac{\omega}{U_{convect}}$$

Here k is the wave number, defined as $k=2\pi/\lambda$ and has units of 1/length, $\omega$ is the temporal frequency in rad/sec, and $U_{convect}$ is the convection velocity. Thus, the shorter the wavelength (larger k) is, the higher the temporal frequency.

Figure 8:
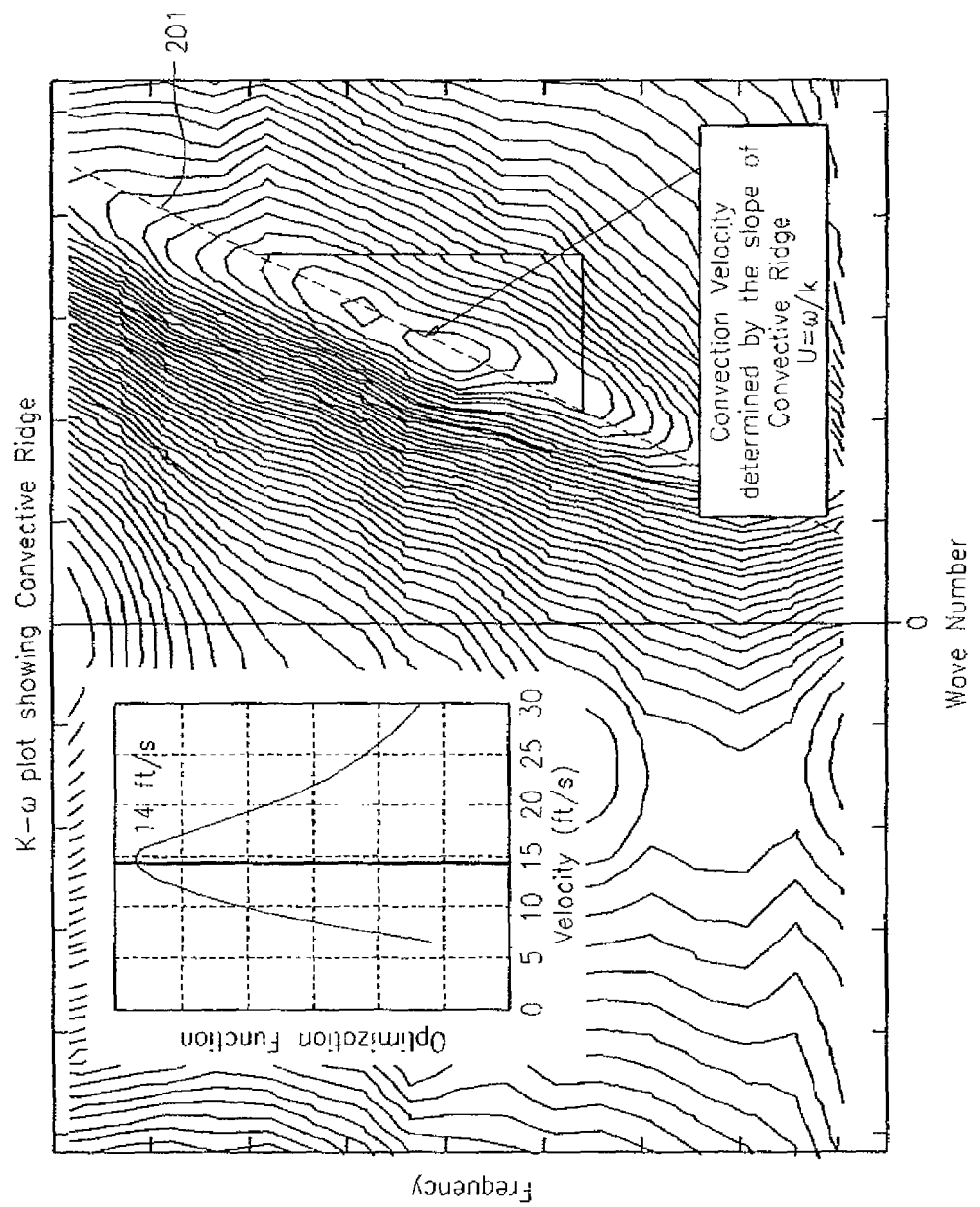
FIG. 8 is a k-ω plot that illustrates the slope of the convective ridge, and a plot of the optimization function of the convective ridge.

Now referring to FIG. 8, in sonar array processing, the spatial/temporal frequency content of time stationary sound fields are often displayed using "k-$\omega$ plots". K-$\omega$ plots are essentially three-dimensional power spectra in which the power of a sound field is decomposed into bins corresponding to specific spatial wave numbers and temporal frequencies. On a k-$\omega$ plot, the power associated with a pressure field convecting with the flow is distributed in regions, which satisfies the dispersion relationship developed above. This region is termed "the convective ridge" 201 (Beranek, 1992) and the slope of this ridge on a k-$\omega$ plot indicates the convective velocity of the pressure field. This suggests that the convective velocity of turbulent eddies, and hence flow rate within a pipe 14, can be determined by constructing a k-$\omega$ plot from the output of a phased array of sensor and identifying the slope of the convective ridge 201.

FIG. 8 shows an example of a k-$\omega$ plot generated from a phased array of pressure sensors. The power contours show a well-defined convective ridge. A parametric optimization method was used to determine the "best" line representing the slope of the convective ridge 201. For this case, a slope of 14.2 ft/sec was determined. The intermediate result of the optimization procedure is displayed in the insert, showing that optimized value is a unique and well-defined optima. The k-$\omega$ plot shown in FIG. 8 illustrates the fundamental principle behind sonar based flow measure, namely that axial arrays of pressure sensors can be used in conjunction with sonar processing techniques to determine the speed at which naturally occurring turbulent eddies convect within a pipe.

Figure 9:
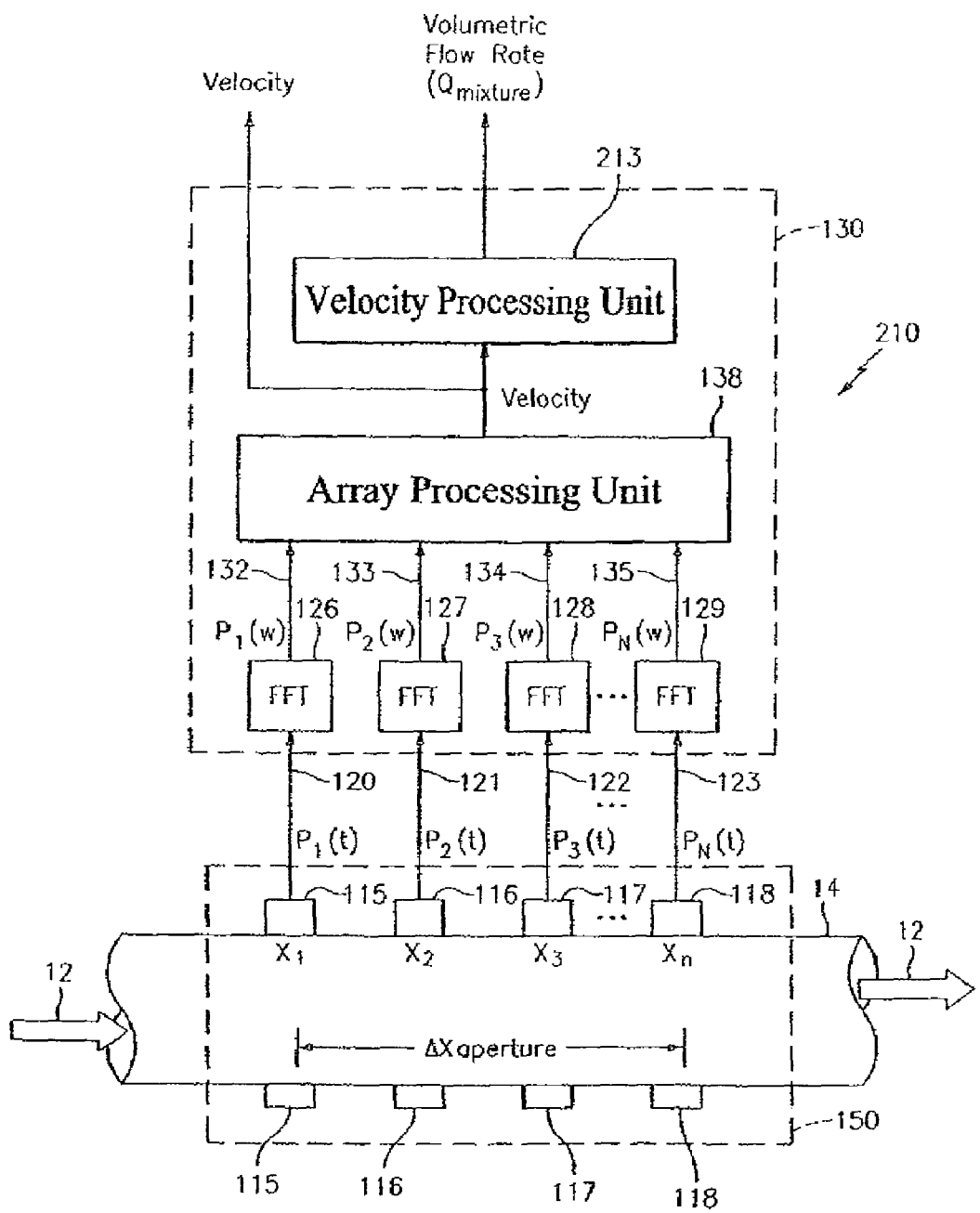
FIG. 9 is a block diagram for an apparatus for measuring the vortical field of a process flow within a pipe, in accordance with the present invention.

As shown in FIG. 9, the array processing unit 138 of the flow meter 210 processes the input pressure signals $P_1(\omega)$-$P_N(\omega)$ to define the convective ridge 201 (see FIG. 8) in the k-$\omega$ plane. The slope of the ridge determines the velocity of the aerated fluid or mixture 12. A velocity processing determines the volumetric flow rate of the aerated fluid 12 using the relationship of: Volumetric Flow Rate–Velocity (Cross-sectional Area of Pipe).

Figure 10:
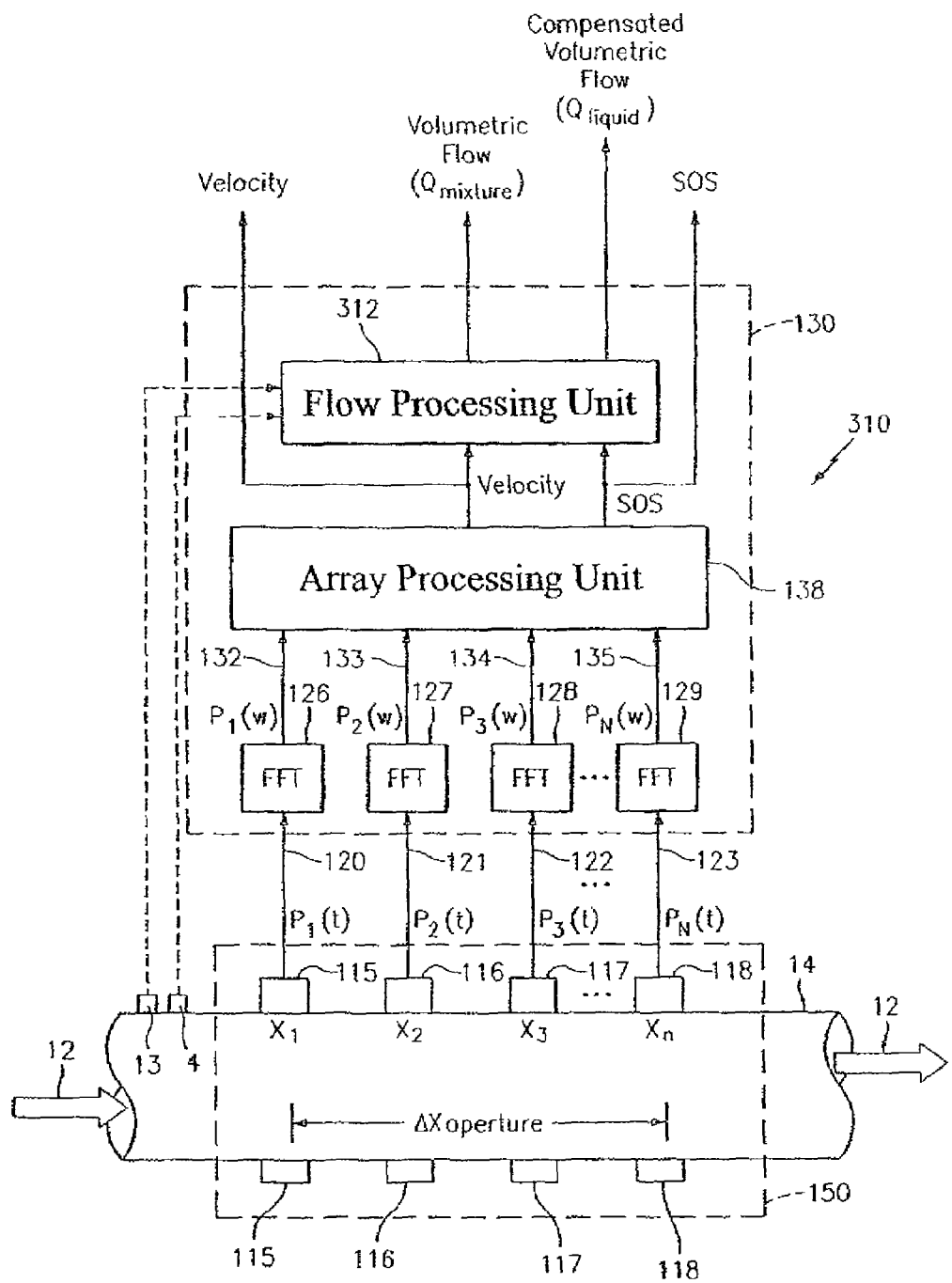
FIG. 10 is a block diagram for an apparatus for measuring the vortical field and acoustic field of a process flow within a pipe, in accordance with the present invention.

While two separate apparatus 110 (FIG. 6) and 210 (FIG. 9) may be used to measure the gas volume fraction and flow velocity, respectively, of the fluid having entrained gas therein to determine the compensated volumetric flow rate, the present invention contemplates a single array of sensors and processing unit may be used to perform both functions as suggested hereinbefore. Such an apparatus 310 is shown in FIG. 10, wherein a single array of pressure sensors 115-118 is used to determine both the speed of sound within the fluid and the flow velocity of the fluid. The flow processing unit 312 combines the functionality of the entrained air processing unit 142 of FIG. 6 and the velocity processing unit 213 of FIG. 9 to provide a compensated volumetric flow measurement.

Figure 11:
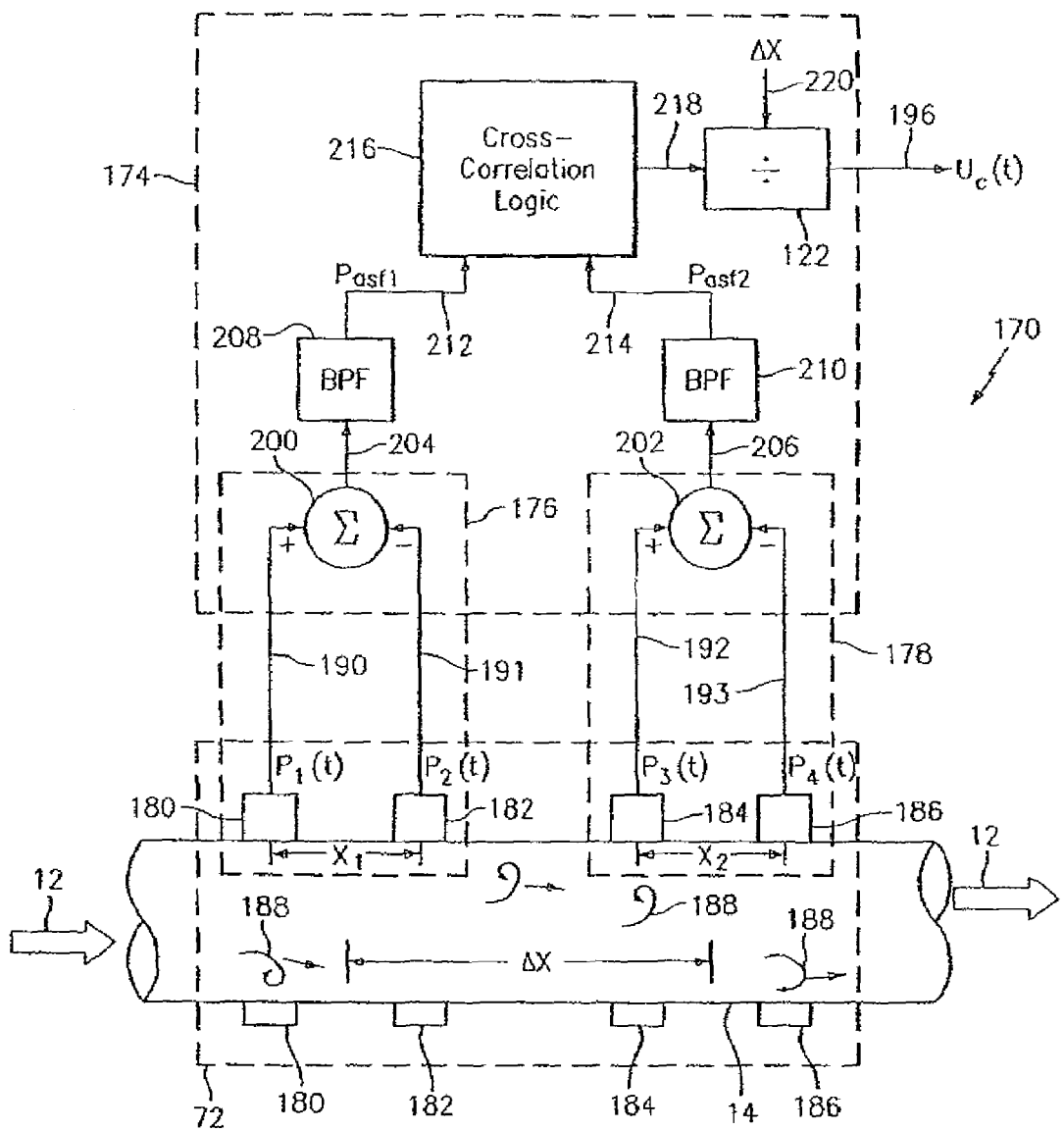
FIG. 11 is a block diagram of another apparatus for measuring the vortical field of a process flow within a pipe, in accordance with the present invention.

Referring to FIG. 11, the second technique of determining the convection velocity of the vortical disturbances within the flow 12 involves cross-correlating unsteady pressure variations using an array of unsteady pressure sensors. The apparatus 170 includes a sensing section 172 along a pipe 14 and a signal processing unit 174. The pipe 14 has two measurement regions 176, 178 located a distance ΔX apart along the pipe 14. At the first measurement region 176 are two unsteady (or dynamic or ac) pressure sensors 180, 182, located a distance $X_1$ apart, capable of measuring the unsteady pressure in the pipe 14, and at the second measurement region 178, are two other unsteady pressure sensors 184, 186, located a distance $X_2$ apart, capable of measuring the unsteady pressure in the pipe 14. Each pair of pressure sensors 180, 182 and 184, 186 act as spatial filters to remove certain acoustic signals from the unsteady pressure signals, and the distances $X_1$, $X_2$ are determined by the desired filtering characteristic for each spatial filter, as discussed hereinafter. It is within the scope of the present invention that the pressure sensor spacing may be known or arbitrary and that as few as two sensors are required if certain information is known about the acoustic properties of the system as will be more fully described herein below.

The apparatus 170 of the present invention measures velocities associated with unsteady flow fields and/or pressure disturbances 188 (e.g., turbulent eddies), inhomogeneities in the flow, or any other properties of the flow, liquid, vapor, or pressure, having time varying or stochastic properties that are manifested at least in part in the form of unsteady pressures (described above). The flow generated vortical flow fields generally increase with mean flow velocity and do not occur at any predeterminable frequency.

As stated above, the vortical pressure disturbances 188, which contain information regarding convection velocity, have temporal and spatial length scales as well as coherence length scales that differ from other disturbances in the flow. The present invention utilizes these properties to preferentially select disturbances of a desired axial length scale and coherence length scale. The terms vortical flow field and vortical pressure field are used herein to describe the above-described group of unsteady pressure fields having temporal and spatial length and coherence scales described herein.

Some or all of the functions within the signal processing unit 174 may be implemented in software (using a microprocessor or computer) and/or firmware, or may be implemented using analog and/or digital hardware, having sufficient memory, interfaces, and capacity to perform the functions described herein.

In the processing unit 174, for example, the pressure signal $P_1(t)$ on the line 190 may be provided to a positive input of a summer 200 and the pressure signal $P_2(t)$ on the line 191 is provided to a negative input of the summer 200. The output of the summer 200 may be provided to line 204 indicative of the difference between the two pressure signals $P_1$, $P_2$ (e.g., $P_1-P_2=P_{as1}$).

The pressure sensors 180, 182 together with the summer 200 create a spatial filter 176. The line 204 is fed to bandpass filter 208, which passes a predetermined passband of frequencies and attenuates frequencies outside the passband. In accordance with the present invention, the passband of the filter 208 is set to filter out (or attenuate) the dc portion and the high frequency portion of the input signals and to pass the frequencies therebetween. Other passbands may be used in other embodiments, if desired. Passband filter 208 provides a filtered signal $P_{asf1}$ on a line 212 to Cross-Correlation Logic 216, described hereinafter.

The pressure signal $P_3(t)$ on the line 192 is provided to a positive input of a summer 202 and the pressure signal $P_4(t)$ on the line 193 is provided to a negative input of the summer 202. The pressure sensors 83, 84 together with the summer 202 create a spatial filter 178. The output of the summer 202 is provided on a line 206 indicative of the difference between the two pressure signals $P_3$, $P_4$ (e.g., $P_3-P_4=P_{as2}$). The line 206 is fed to a bandpass filter 210, similar to the bandpass filter 108 discussed hereinbefore, which passes frequencies within the passband and attenuates frequencies outside the passband. The filter 210 provides a filtered signal $P_{asf}$ on a line 214 to the Cross-Correlation Logic 216. The signs on the summers 200, 202 may be swapped if desired, provided the signs of both summers are swapped together. In addition, the pressure signals $P_1$, $P_2$, $P_3$, $P_4$ may be scaled prior to presentation to the summers 200, 202.

The Cross-Correlation Logic 216 calculates a known time domain cross-correlation between the signals $P_{asf1}$ and $P_{asf2}$ on the lines 212, 214, respectively, and provides an output signal on a line 218 indicative of the time delay τ it takes for an vortical flow field 188 (or vortex, stochastic, or vortical structure, field, disturbance or perturbation within the flow) to propagate from one sensing region 176 to the other sensing region 178. Such vortical flow disturbances, as is known, are coherent dynamic conditions that can occur in the flow which substantially decay (by a predetermined amount) over a predetermined distance (or coherence length) and convect (or flow) at or near the average velocity of the fluid flow. As described above, the vortical flow field also has a stochastic or vortical pressure disturbance associated with it. In general, the vortical flow disturbances 188 are distributed throughout the flow, particularly in high shear regions, such as boundary layers (e.g., along the inner wall of the tube 14) and are shown herein as discrete vortical flow fields. Because the vortical flow fields (and the associated pressure disturbance) convect at or near the mean flow velocity, the propagation time delay τ is related to the velocity of the flow by the distance ΔX between the measurement regions 176, 178, as discussed hereinafter.

The present invention uses temporal and spatial filtering to precondition the pressure signals to effectively filter out the acoustic pressure disturbances $P_{acoustic}$ and other long wavelength (compared to the sensor spacing) pressure disturbances in the tube 14 at the two sensing regions 176, 178 and retain a substantial portion of the vortical pressure disturbances $P_{vortical}$ associated with the vortical flow field and any other short wavelength (compared to the sensor spacing) low frequency pressure disturbances $P_{other}$. In accordance with the present invention, if the low frequency pressure disturbances $P_{other}$ are small, they will not substantially impair the measurement accuracy of $P_{vortical}$.

One or more of the above-described apparatus embodiments 10, 110, 210, 310 of a sonar-based flow meter can be used to identify the product(s) passing through the pipe. As stated above, with the knowledge that certain fluids (e.g., refined liquid hydrocarbons) have well characterized sound speeds, the present invention measures the speed of sound propagating through the fluid to determine (i.e., identify) the fluid (i.e., product) flowing through the pipe. With knowledge of the pressure and temperature of the process fluid, a measurement of the sound speed of the process fluid enables the determination of the type of product flowing through the meter.

The invention involves the inclusion of a data base (e.g., a look-up table) to relate the measured sound speed, along with pressure and temperature values, into the output of a SONAR-based volumetric flow and sound speed monitor to provide rate and product type identification. The ability of the invention to provide product type information is advantageous not only for fluid flow consisting of a particular product, but also for fluid flow consisting of more than one product. For example, if an operation changes processing one known product to another, the present invention can be configured to provide an estimate of the phase fraction of the two components within a pipe via the Wood Equations. Consequently, the apparatus 10 is operable to determine when and how fast it takes for an operation to transition from a first fluid to a second fluid within a pipe. It is anticipated that the real time feedback including product flow rate (including direction) and type will enable more efficient operation of facilities that transport, store, and distribute different fluids (e.g., refined hydrocarbons).

Figure 12:
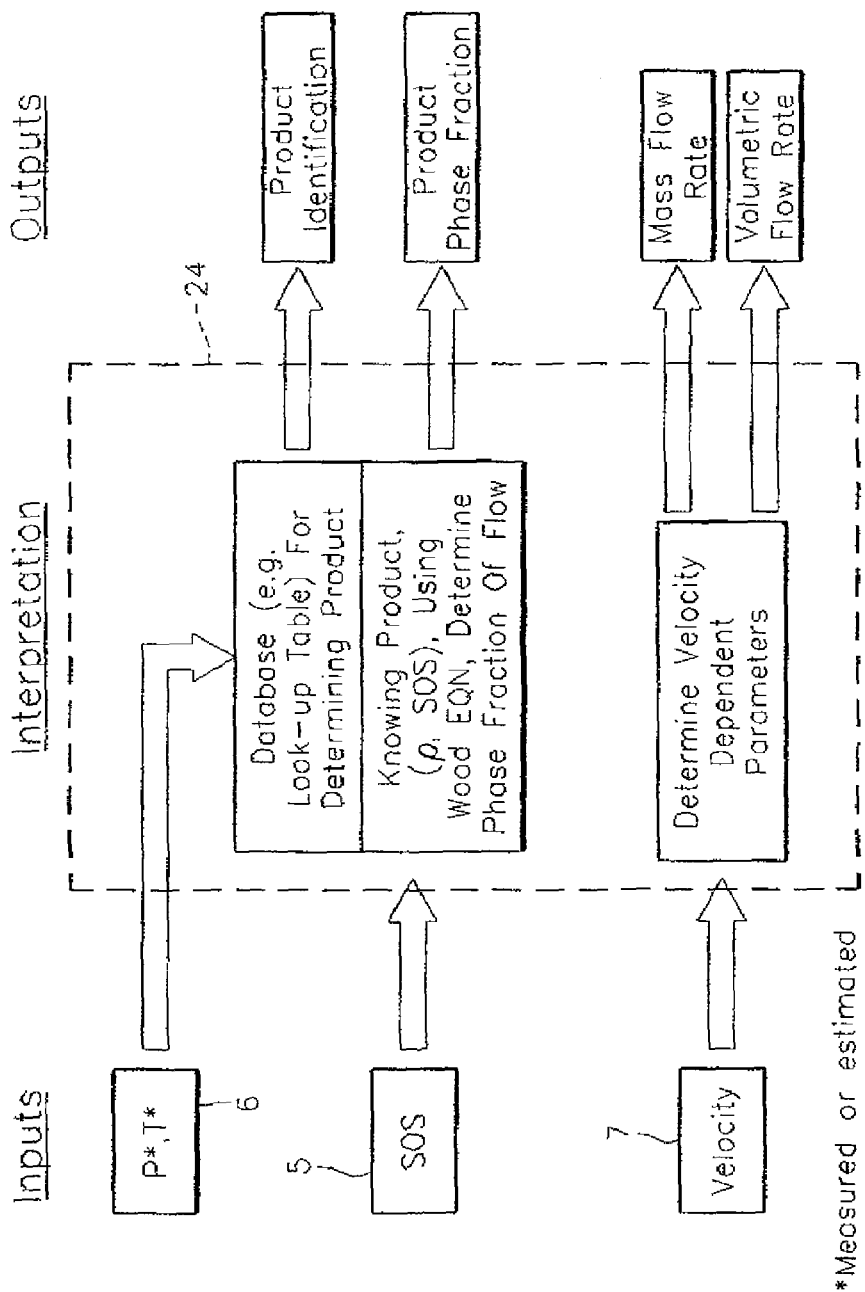
FIG. 12 is a functional flow diagram of an apparatus embodying the present invention.
Figure 13:
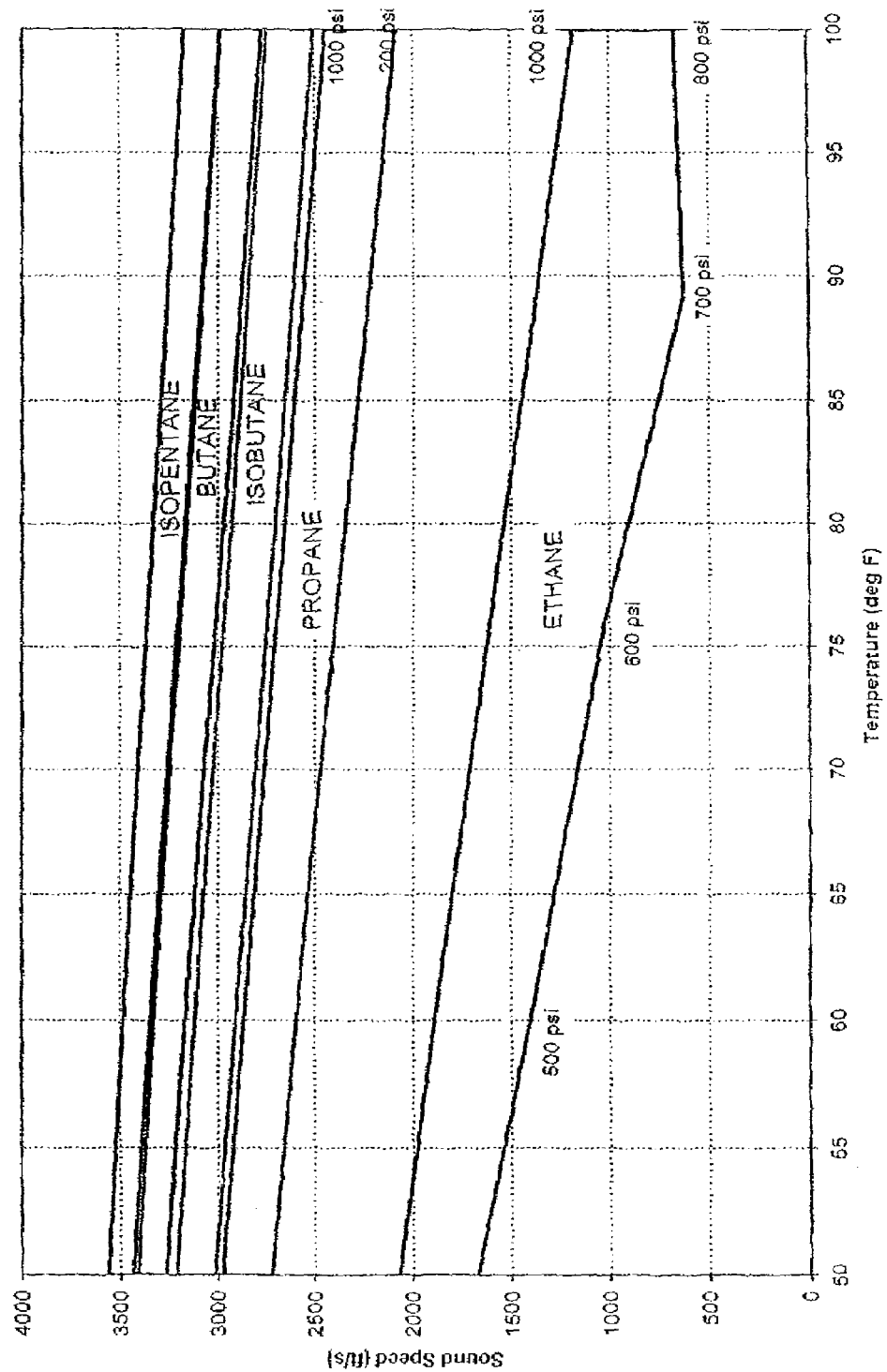
FIG. 13 is a plot of five (5) potential fluids in the form of a liquid passing through a pipe, whereby the speed of sound of each fluid is shown as a function temperature, and pressure, in accordance with the present invention.

FIG. 12 illustrates a block diagram of the processor 24 for determining the mass flow rate and/or the volumetric flow of the fluid using the determined velocity of the fluid. Further, the processor determines the product identification look up tables that provide the identification of the product as a function of the speed of sound (SOS), pressure and temperature of the fluid. The relationship of these parameters of the fluid as a function of the fluids identification is shown in FIG. 13. As shown, the identity of the fluid in the pipe can be determined knowing the pressure, temperature, and SOS of the fluid when the possible types of fluids flowing within the pipes are known. The information shown in FIG. 13 can be stored in a look-up table (or other storage configuration) which can be accessed by the processor.

Figure 14:
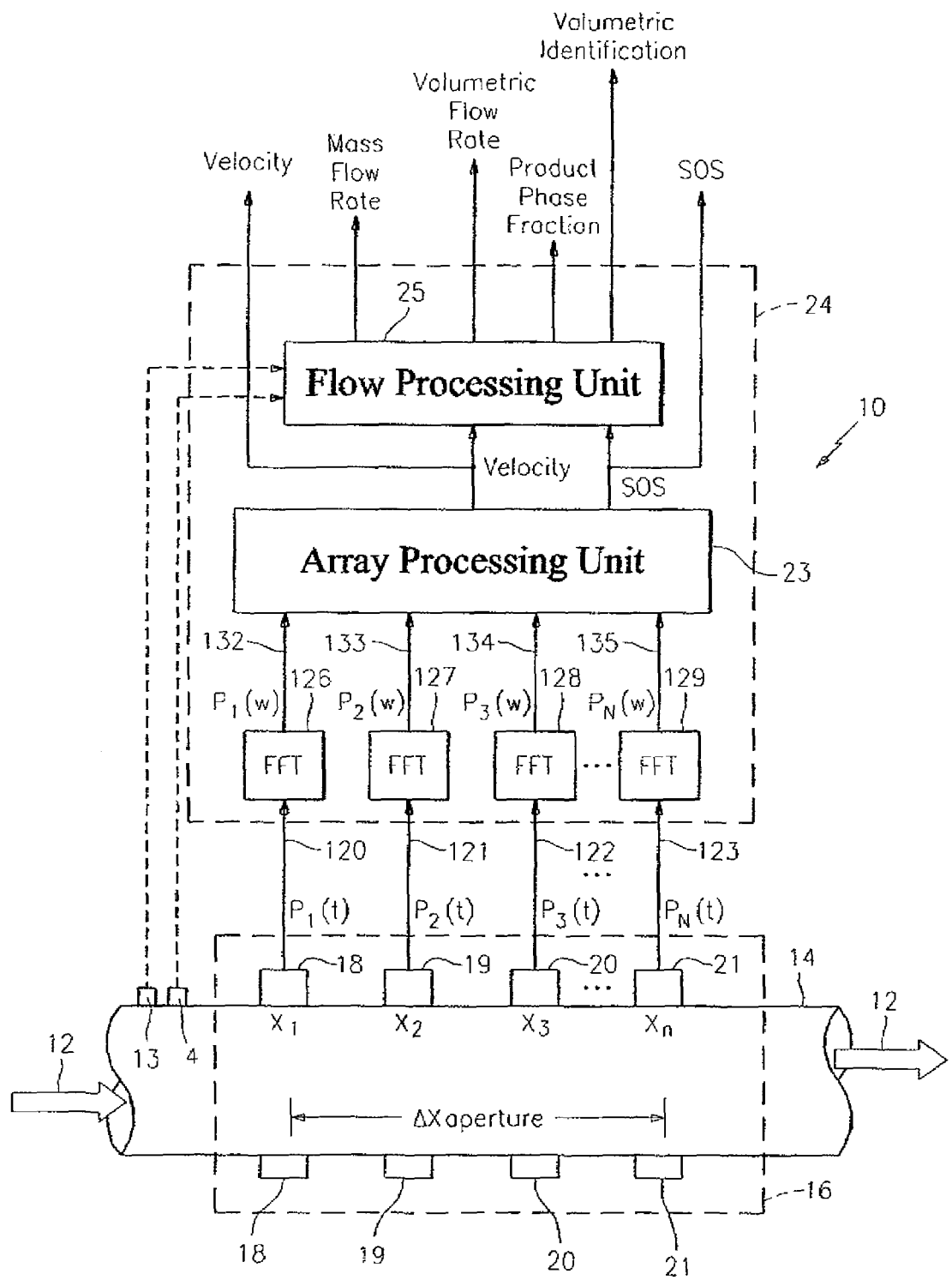
FIG. 14 is a more detailed schematic diagram of an apparatus similar to that shown in FIGS. 1 and 4, in accordance to the present invention.
Figure 15:
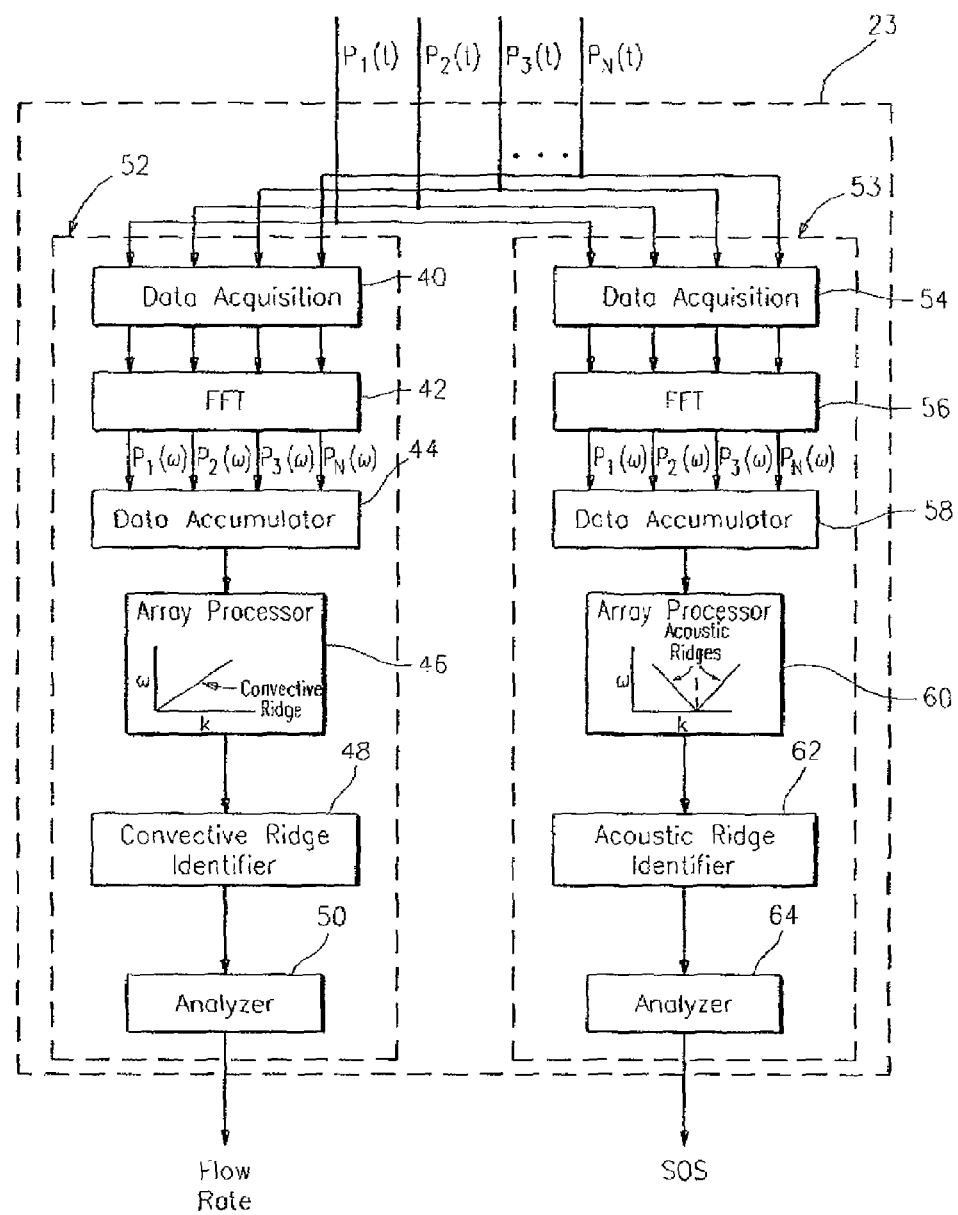
FIG. 15 is a block diagram of a velocity logic and a speed of sound logic of an array processing unit of the apparatus of FIGS. 1, 4 and 14, in accordance with the present invention.

FIG. 14 illustrates a more detailed embodiment of the present invention in a manner similar to the apparatus 10, 310 schematics disclosed above (e.g., FIG. 10). In this embodiment, the processor 24 includes an array processing unit 23 for determining the velocity and SOS of the fluid, and a flow processing unit 25 for determining at least one of the mass flow rate, volumetric flow rate, fluid identification, and the phase fraction of the fluid. FIG. 15 illustrates the steps for determining the flow rate and SOS of the fluid. A detailed explanation of these processing steps is provided above, and can also be found in the U.S. patents and applications reference hereinbefore, and also in U.S. Pat. Nos. 6,587,798 and 6,609,069, which are incorporated herein by reference. FIGS. 7 and 8 are plots of the convective ridge and acoustic ridges, respectively, for determining the velocity and SOS of the fluid.

Figure 16:
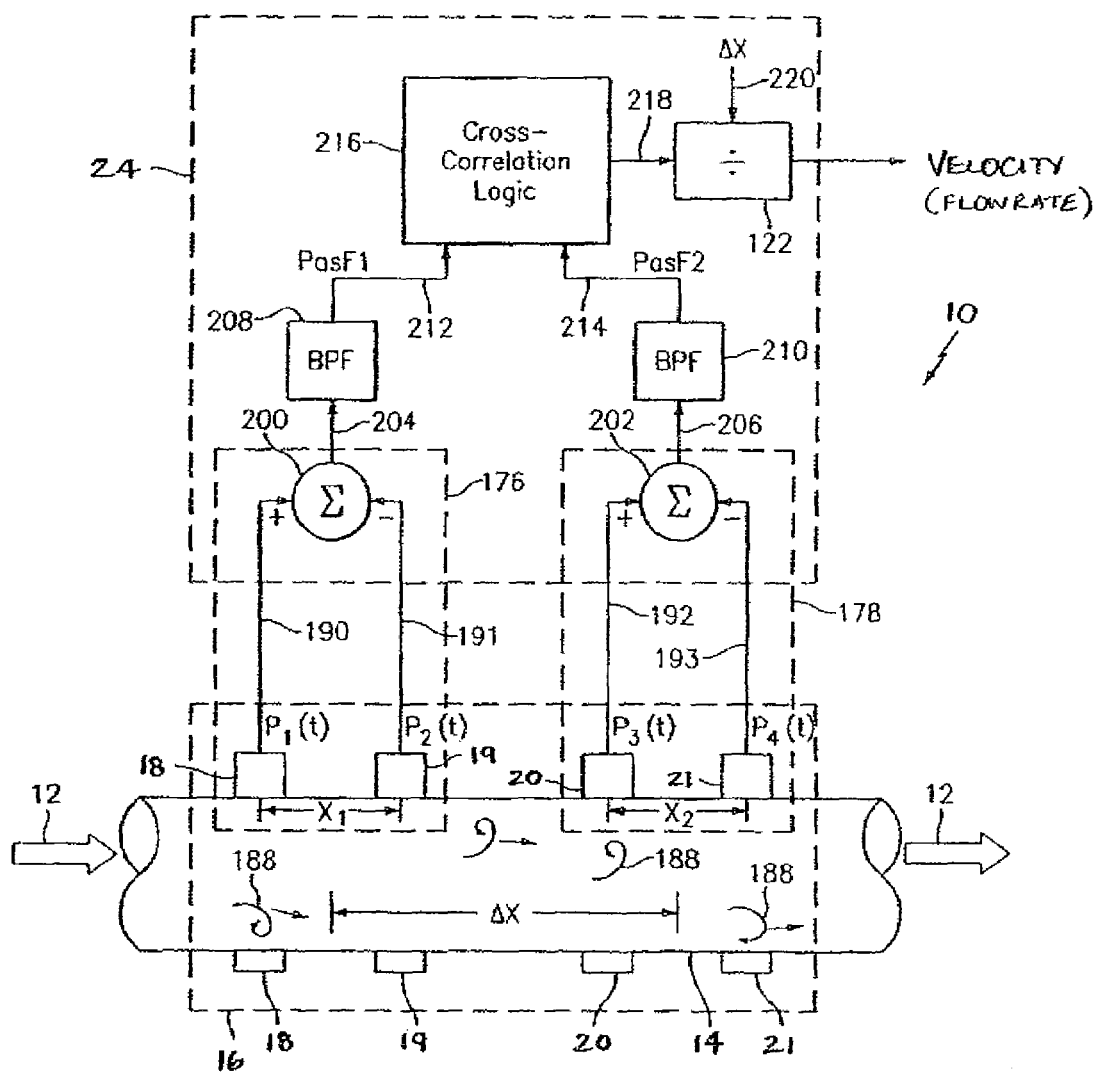
FIG. 16 is schematic diagram of an embodiment of an apparatus, wherein the velocity of the fluid flow is determined using a cross-correlation technique.

FIG. 16 illustrates another detailed embodiment of the present invention similar to the apparatus 10, 170 schematically disclosed in FIG. 11, wherein the velocity of the fluid flow is determined using a cross-correlation technique. A detailed explanation of the identified processing steps is provided above, and can also be found in the U.S. Patent Publication No. 2004/0168523, which is incorporated herein by reference.

The invention further contemplates that the output of the apparatus may be used to control valves and pumps to enable the user to better control the transfer and/or processing the fluid mixture. The invention contemplates that a plurality of apparatus embodying the present invention may be used at different locations in the process to enable the user to identify what fluid is in each pipe in the flow process as well as the volumetric flow rate (and other parameters) of the fluid at the specific location.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof Therefore, it is intended that the invention not be limited to the particular embodiment(s) disclosed herein as the best mode contemplated for carrying out this invention.

What is claimed is:

1. An apparatus for identifying one or more fluid products flowing within a pipe, comprising:
   a flow meter having a plurality of sensors operable to detect vortical disturbances flowing with the fluid products and acoustic waves propagating through the fluid products and create signals indicative of the vortical disturbances and acoustic waves, which flow meter is mounted on the pipe; and
   a processing unit operable to determine the speed of sound and volumetric flow rate of the one or more fluid products using the signals from the flow meter, wherein the processing unit includes a database having speed of sound data for a predetermined group of products, and further wherein the processing unit is operable to identify the type of each product flowing within the pipe given a temperature and pressure value of the products within the pipe.

2. The apparatus of claim 1, wherein the database contains speed of sound data as a function of temperature and pressure of the products within the pipe.

3. The apparatus of claim 2, wherein the database is a look-up table.

4. The apparatus of claim 1, wherein the processing unit is operable to determine the volumetric flow rate by determining convection velocity of vortical disturbances within the flow of one or more fluid products, and wherein the convection velocity is determined by characterizing a convective ridge representing vortical disturbances within the flow.

5. The apparatus of claim 1, wherein the processing unit is operable to determine the volumetric flow rate by determining convection velocity of vortical disturbances within the flow of one or more fluid products, and wherein the convection velocity is determined by cross-correlating unsteady pressure variations.

6. An apparatus for identifying one or more fluid products flowing within a pipe, comprising:
   a flow meter having a plurality of sensors, each sensor having a transmitting portion for transmitting ultrasonic signals and a receiving portion for receiving the ultrasonic signals, which flow meter is mounted on the pipe; and
   a processing unit operable to determine a transit time of the ultrasonic signals between the transmitting portion and the receiving portion of each sensor, and utilize such transit times to determine the speed of sound and volumetric flow rate of the one or more fluid products;
   wherein the processing unit includes a database having speed of sound data for a predetermined group of fluid products, and the processing unit is operable to identify the type of each product flowing within the pipe given a temperature and pressure value of the products within the pipe.

7. The apparatus of claim 6, wherein the transit times are indicative of coherent disturbances propagating through the flow of fluid products.

8. The apparatus of claim 6, wherein the transit times are indicative of coherent disturbances convecting with the flow of fluid products.

9. The apparatus of claim 8, wherein the transmitting portion and receiving portion of each sensor are mounted on the pipe so that the ultrasonic signals travel normal to an axial centerline of the pipe.

10. The apparatus of claim 8, wherein the transmitting portion and receiving portion of each sensor are mounted in a pulse/echo configuration.

11. The apparatus of claim 8, wherein the transmitting portion and receiving portion of each sensor are mounted on the pipe axially spaced apart from one another on a same side of the pipe.

12. A method for identifying one or more fluid products flowing within a pipe, comprising:
   providing a flow meter having a plurality of sensors operable to detect vortical disturbances flowing with the fluid products and acoustic waves propagating through the fluid products, and a processing unit having a database containing speed of sound data for a predetermined group of products as a function of temperature and pressure;
   determining a speed of sound for each of the one or more fluid products using a k-ω plot based on first signals from the flow meter representative of acoustic waves propagating through the flow;
   determining a convection velocity of the vortical disturbances within the flow based on the second signals from the flow meter representative of vortical disturbances flowing with the one or more fluid products;
   identifying a type of each product using the determined speed of sound for a given temperature and pressure value of the products within the pipe.

13. The method of claim 12, further comprising the step of determining a volumetric flow rate of the one or more products using the convection velocity.

14. The method of claim 13, wherein the database is a look-up table.

15. The method of claim 12, wherein the convection velocity of the vortical disturbances within the flow is determined using a k-ω plot.

16. The method of claim 12, wherein the convection velocity is determined by cross-correlating unsteady pressure variations.

17. A method for identifying one or more fluid products flowing within a pipe, comprising:
   providing a flow meter having a plurality of sensors, each sensor having a transmitting portion and a receiving portion, which flow meter is mounted on the pipe, and a processing unit having a database containing speed of sound data for a predetermined group of products as a function of temperature and pressure;
   transmitting ultrasonic signals between the transmitting and receiving portions of each sensor;
   determining transit times of the ultrasonic signals traveling between the transmitting and receiving portions of each sensor, and utilizing such transit times to determine the speed of sound and volumetric flow rate of the one or more fluid products;
   identifying a type of each product using the determined speed of sound for a given temperature and pressure value of the products within the pipe.

18. The method of claim 17, wherein the transmitting portion and receiving portion of each sensor are mounted on the pipe so that the ultrasonic signals travel normal to an axial centerline of the pipe.

19. The method of claim 17, wherein the database is a look-up table.

* * * * *